(12) United States Patent
Lou et al.

(10) Patent No.: US 11,371,099 B2
(45) Date of Patent: Jun. 28, 2022

(54) HEATR1 AS A MARKER FOR CHEMORESISTANCE

(71) Applicant: MAYO FOUNDATION FOR MEDICAL EDUCATION AND RESEARCH, Rochester, MN (US)

(72) Inventors: Zhenkun Lou, Rochester, MN (US); Tongzheng Liu, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 568 days.

(21) Appl. No.: 15/780,074

(22) PCT Filed: Nov. 16, 2016

(86) PCT No.: PCT/US2016/062298
§ 371 (c)(1),
(2) Date: May 30, 2018

(87) PCT Pub. No.: WO2017/095632
PCT Pub. Date: Jun. 8, 2017

(65) Prior Publication Data
US 2018/0346991 A1 Dec. 6, 2018

Related U.S. Application Data

(60) Provisional application No. 62/260,904, filed on Nov. 30, 2015.

(51) Int. Cl.
| | | |
|---|---|---|
| *C12Q 1/6886* | (2018.01) | |
| *G01N 33/574* | (2006.01) | |
| *C12Q 1/68* | (2018.01) | |
| *A61P 35/00* | (2006.01) | |
| *A61K 31/7064* | (2006.01) | |
| *A61K 31/7068* | (2006.01) | |

(52) U.S. Cl.
CPC ........ *C12Q 1/6886* (2013.01); *A61K 31/7064* (2013.01); *A61K 31/7068* (2013.01); *A61P 35/00* (2018.01); *C12Q 1/68* (2013.01); *G01N 33/57438* (2013.01); *C12Q 2600/106* (2013.01); *C12Q 2600/158* (2013.01); *G01N 2333/91215* (2013.01); *G01N 2800/52* (2013.01)

(58) Field of Classification Search
CPC ........ C12Q 2600/106; G01N 2800/52; G01N 33/57438; A61P 35/00
See application file for complete search history.

(56) References Cited

U.S. PATENT DOCUMENTS

| | | | |
|---|---|---|---|
| 8,828,451 B2 | 9/2014 | Sebti et al. | 514/183 |
| 2013/0079241 A1 | 3/2013 | Luo et al. | 506/7 |
| 2014/0199404 A1 | 7/2014 | Heise | 424/491 |
| 2014/0243403 A1 | 8/2014 | Singh et al. | 514/450 |
| 2014/0342946 A1 | 11/2014 | Kuriakose et al. | 435/6.1 |

FOREIGN PATENT DOCUMENTS

| | | |
|---|---|---|
| WO | WO/2006/119980 | 11/1906 |
| WO | WO/2009/032651 | 3/1909 |
| WO | WO/2012/142330 | 10/1912 |
| WO | WO/2013/098797 | 7/1913 |
| WO | WO/2014/151117 | 9/1914 |
| WO | WO/20 14/160499 | 10/1914 |
| WO | WO/2015/063302 | 5/1915 |

OTHER PUBLICATIONS

Kim et al (Anticancer Research, Sep. 2015, vol. 35, pp. 4599-4604) (Year: 2015).*
Yamamoto et al (Clinical Cancer Research, 2004, vol. 10, pp. 2846-2850). (Year: 2004).*
Alessi, D. R. et al. (1997) "Characterization of a 3-phosphoinositide-dependent protein kinase which phosphorylates and activates protein kinase Bα," *Current Biology* 7(4), 261-269.
Altomare, D. A. et al. (2005) "Perturbations of the AKT signaling pathway in human cancer," *Oncogene* 24, 7455.
Azuma, M. et al. (2006) "Perturbation of rRNA Synthesis in the bap28 Mutation Leads to Apoptosis Mediated by p53 in the Zebrafish Central Nervous System," *Journal of Biological Chemistry* 281(19), 13309-13316.
Bellacosa, A. et al. (2005) "Activation of AKT Kinases in Cancer: Implications for Therapeutic Targeting," in *Advances in Cancer Research*, pp. 29-86, Academic Press.
Berndt, N. et al. (2010) "The Akt activation inhibitor TCN-P inhibits Akt phosphorylation by binding to the PH domain of Akt and blocking its recruitment to the plasma membrane," *Cell Death and Differentiation* 17(11), 1795-1804.
Boreddy, S. R. et al. (2011) "Pancreatic Tumor Suppression by Benzyl Isothiocyanate Is Associated with Inhibition of PI3K/AKT/FOXO Pathway," *Clinical Cancer Research* 17(1), 1784.
Brazil, D. P. et al. (2001) "Ten years of protein kinase B signalling: a hard Akt to follow," *Trends in Biochemical Sciences* 26(11), 657-664.
Brognard, J. et al. (2007) "PHLPP and a Second Isoform, PHLPP2, Differentially Attenuate the Amplitude of Akt Signaling by Regulating Distinct Akt Isoforms," *Molecular Cell* 25(6), 917-931.
Brunet, A. et al. (1999) "Akt Promotes Cell Survival by Phosphorylating and Inhibiting a Forkhead Transcription Factor," *Cell* 96(6), 857-868.
Carthew, R. W. (2001) "Gene silencing by double-stranded RNA," *Current Opinion in Cell Biology* 13(2), 244-248.

(Continued)

*Primary Examiner* — Karen A. Canella
(74) *Attorney, Agent, or Firm* — Medlen & Carroll, LLP

(57) ABSTRACT

The present invention relates to methods of using HEATR1 expression levels for guiding chemotherapy treatment of pancreatic cancer. In particular, measuring lower HEATR1 expression in pancreatic cancer is associated with resistance to the use of certain chemotherapy treatments such that by changing the treatment a better prognosis may be obtained for the patient. Further, lower HEATR1 expression is related to a poorer long-term prognosis of pancreatic cancer patients thus measuring an increase or maintenance/decrease during treatment may be useful for predicting treatment response.

8 Claims, 11 Drawing Sheets

(56) References Cited

OTHER PUBLICATIONS

Chan, C.-H. et al. (2012) "The Skp2-SCF E3 Ligase Regulates Akt Ubiquitination, Glycolysis, Herceptin Sensitivity, and Tumorigenesis," *Cell* 149(5), 1098-1111.

Chen, D. et al. (2012) "Inhibition of AKT2 Enhances Sensitivity to Gemcitabine via Regulating PUMA and NF-κB Signaling Pathway in Human Pancreatic Ductal Adenocarcinoma," *International Journal of Molecular Sciences* 13(1), 1186-1208.

Costello, E. et al. (2012) "New biomarkers and targets in pancreatic cancer and their application to treatment," *Nature Reviews Gastroenterology & Hepatology* 9, 435.

Cross, D. A. E. et al. (1995) "Inhibition of glycogen synthase kinase-3 by insulin mediated by protein kinase B," *Nature* 378, 785.

Datta, S. R. et al. (1997) "Akt Phosphorylation of BAD Couples Survival Signals to the Cell-Intrinsic Death Machinery," *Cell* 91(2), 231-241.

Dima, S. O. et al. (2012) "An exploratory study of inflammatory cytokines as prognostic biomarkers in patients with ductal pancreatic adenocarcinoma," *Pancreas* 41(7), 1001-1007.

Fahy, B. N. et al. (2003) "AKT inhibition is associated with chemosensitisation in the pancreatic cancer cell line MIA-PaCa-2," *British Journal of Cancer* 89, 391.

Gao, T. et al. (2005) "PHLPP: A Phosphatase that Directly Dephosphorylates Akt, Promotes Apoptosis, and Suppresses Tumor Growth," *Molecular Cell* 18(1), 13-24.

Groves, M. R. et al. (1999) "The Structure of the Protein Phosphatase 2 A PR65/A Subunit Reveals the Conformation of Its 15 Tandemly Repeated HEAT Motifs," *Cell* 96(1), 99-110.

Haar, E. V. et al. (2007) "Insulin signalling to mTOR mediated by the Akt/PKB substrate PRAS40," *Nature Cell Biology* 9, 316.

Happo, L. et al. (2010) "Maximal killing of lymphoma cells by DNA damage-inducing therapy requires not only the p53 targets Puma and Noxa, but also Bim," *Blood* 116(24), 5256.

Hu, C. et al. (2015) "Combined Inhibition of Cyclin-Dependent Kinases (Dinaciclib) and AKT (MK-2206) Blocks Pancreatic Tumor Growth and Metastases in Patient-Derived Xenograft Models," *Molecular Cancer Therapeutics* 14(7), 1532.

Jazirehi, A. R. et al. (2012) "Therapeutic implications of targeting the PI3Kinase/AKT/mTOR signaling module in melanoma therapy," *American Journal of Cancer Research* 2(2), 178-191.

Kuo, Y.-C. et al. (2008) "Regulation of Phosphorylation of Thr-308 of Akt, Cell Proliferation, and Survival by the B55α Regulatory Subunit Targeting of the Protein Phosphatase 2A Holoenzyme to Akt," *Journal of Biological Chemistry* 283(4), 1882-1892.

Li, L. et al. (2008) "Gemcitabine and Cytosine Arabinoside Cytotoxicity: Association with Lymphoblastoid Cell Expression," *Cancer Research* 68(17), 7050.

Liu, T. et al. (2016) "HEATR1 Negatively Regulates Akt to Help Sensitize Pancreatic Cancer Cells to Chemotherapy," *Cancer Research* 76(f), 572.

Manning, B. D. et al. (2007) "AKT/PKB Signaling: Navigating Downstream," *Cell* 129(7), 1261-1274.

Meuillet, E. J. et al. (2010) "Molecular Pharmacology and Antitumor Activity of PHT-427, a Novel Akt/Phosphatidylinositide-Dependent Protein Kinase 1 Pleckstrin Homology Domain Inhibitor," *Molecular Cancer Therapeutics* 9(3), 706.

Misek, D. E. et al. (2007) "Early Detection and Biomarkers in Pancreatic Cancer," *Journal of the National Comprehensive Cancer Network* 5(10), 1034-1041.

Mortenson, m. m. et al. (2004) "AKT: A novel target in pancreatic cancer therapy," *Cancer Therapy* 2, 227-238.

Neuwald, A. F. et al. (2000) "HEAT Repeats Associated with Condensins, Cohesins, and Other Complexes Involved in Chromosome-Related Functions," *Genome Research* 10(10), 1445-1452.

Padmanabhan, S. et al. (2009) "A PP2A Regulatory Subunit Regulates C. elegans Insulin/IGF-1 Signaling by Modulating AKT-1 Phosphorylation," *Cell* 136(5), 939-951.

Pal, S. K. et al. (2010) "Akt inhibitors in clinical development for the treatment of cancer," *Expert Opinion on Investigational Drugs* 19(11), 1355-1366.

Pei, H. et al. (2009) "FKBP51 Affects Cancer Cell Response to Chemotherapy by Negatively Regulating Akt," *Cancer Cell* 16(3), 259-266.

Peso, L. d. et al. (1997) "Interleukin-3-Induced Phosphorylation of BAD Through the Protein Kinase Akt," *Science* 278(5338), 687.

Rexahn Pharmaceuticals. I. (2009) NCT01028495: A Safety and Efficacy Study of RX-0201 Plus Gemcitabine in Metastatic Pancreatic Cancer.

Rodgers, J. T. et al. (2011) "Clk2 and B56β Mediate Insulin-Regulated Assembly of the PP2A Phosphatase Holoenzyme Complex on Akt," *Molecular Cell* 41(4), 471-479.

Ruvolo, P. P. et al. (2011) "Low Expression Of PP2A Regulatory Subunit B55α Is Associated With T308 Phosphorylation Of AKT And Shorter Complete Remission Duration In Acute Myeloid Leukemia Patients," *Leukemia* 25(11), 1711-1717.

Sambrook, J. et al. (1989) "Transfer and Fixation of Denatured RNA to Membranes," in *Molecular Cloning: A Laboratory Manual* (Sambrook, J., et al., Eds.) 2nd ed., pp. 7.39-.52, Cold Spring Harbor Laboratory Press, New York.

Sarbassov, D. D. et al. (2005) "Phosphorylation and regulation of Akt/PKB by the rictor-mTOR complex," *Science* 507(5712), 1098-1101.

Schlieman, M. G. et al. (2003) "Incidence, mechanism and prognostic value of activated AKT in pancreas cancer," *British Journal of Cancer* 89(11), 2110-2115.

Stathis, A. et al. (2010) "Advanced pancreatic carcinoma: current treatment and future challenges," *Nature Reviews Clinical Oncology* 7, 163.

Wu, Z. B. et al. (2014) "Glioma-Associated Antigen HEATRI Induces Functional Cytotoxic T Lymphocytes in Patients with Glioma," *Journal of Immunology Research* 2014, 12.

Yang, W.-L. et al. (2009) "The E3 Ligase TRAF6 Regulates Akt Ubiquitination and Activation," *Science (New York, N.Y.)* 325(5944), 1134-1138.

Yap, T. A. et al. (2011) "First-in-Man Clinical Trial of the Oral Pan-AKT Inhibitor MK-2206 in Patients With Advanced Solid Tumors," *Journal of Clinical Oncology* 29(35), 4688-4695.

PCT International SearchReport of International Application No. PCT/US2016/062298 dated Mar. 16, 2017.

\* cited by examiner

HEATR1 AS A MARKER FOR CHEMORESISTANCE

CROSS-REFERENCE TO RELATED APPLICATION

The present application claims the benefit of U.S. Provisional Application Ser. No. 62/260,904, filed Nov. 30, 2015, which is incorporated herein by reference.

FIELD OF THE INVENTION

The present invention relates to methods of using HEATR1 expression levels for guiding chemotherapy treatment of pancreatic cancer. In particular, measuring lower HEATR1 expression in pancreatic cancer is associated with resistance to the use of certain chemotherapy treatments such that by changing the treatment a better prognosis may be obtained for the patient. Further, lower HEATR1 expression is related to a poorer long-term prognosis of pancreatic cancer patients thus measuring an increase or maintenance/decrease during treatment may be useful for predicting treatment response.

BACKGROUND

Pancreatic ductal adenocarcinoma (PDAC) is a lethal malignancy. The prognosis of patients with PDAC is dismal with a five-year survival of less than 5%. Anti-tumor drugs and radiation therapy are current treatment options for PDAC, however drug resistance frequently occurs.

Despite efforts, effective early detection markers of PDAC are currently not available and approximately 80% of patients are diagnosed at locally advanced or metastatic stages (29). In these patients at advanced stage, limited response to current treatments results in an extremely poor prognosis (30).

Cancer treatment by chemotherapy mainly induces apoptosis to kill cancer cells. However, failure to activate apoptosis in these cancer cells causes resistance to therapy, which is an important clinical problem in the treatment of cancers.

Thus, improvements in diagnosis and predictability of patient response to existing therapies are urgently needed for PDAC. Furthermore, new targeted therapies for overcoming the resistance of PDAC to chemotherapy are needed.

SUMMARY

The present invention relates to methods of using HEATR1 expression levels for guiding chemotherapy treatment of pancreatic cancer. In particular, measuring lower HEATR1 expression in pancreatic cancer is associated with resistance to the use of certain chemotherapy treatments such that by changing the treatment a better prognosis may be obtained for the patient. Further, lower HEATR1 expression is related to a poorer long-term prognosis of pancreatic cancer patients thus measuring an increase or maintenance/decrease during treatment may be useful for predicting treatment response.

The present invention provides methods for treating pancreatic cancer, in particular, PDAC. However, methods described herein are not limited to PDAC. In fact, these methods are contemplated for use in other cancers, such as breast and ovarian cancer, in particular as related to the use of chemotherapeutics such as oxaliplatin, mitomycin C, SN-38, etoposide Camptothecin and paclitaxel.

Thus, the present invention provides a method, comprising: a) obtaining a tissue a sample from a subject having pancreatic ductal adenocarcinoma cancer and undergoing therapy; b) measuring the level of the heat repeating region 1 (HEATR1) biomarker in said tissue sample; and c) changing said therapy when a lower amount of HEATR1 is detected in said pancreatic cancer cell compared to a control.

The present invention provides a method, comprising: a) obtaining a tissue a sample from a subject having pancreatic ductal adenocarcinoma cancer and undergoing therapy; b) measuring the level of the serine/threonine protein kinase (Akt) 308 (Akt308) phosphorylation biomarker in said tissue sample; and c) changing said therapy when a higher amount of said biomarker is detected in said pancreatic cancer cell compared to a control.

The present invention provides a method, comprising: a) providing a subject having pancreatic ductal adenocarcinoma cancer undergoing therapy with a chemotherapeutic agent; b) detecting resistance to said chemotherapeutic agent; and c) administering a combination therapy of an Akt inhibitor, wherein Akt308 phosphorylation is inhibited, and said chemotherapeutic agent. In one embodiment, said cancer exhibits resistance to Gemcitabine. In one embodiment, said combination therapy comprises Triciribine and Gemcitabine.

(A) PANC-1 and ASPC-1 cells stably expressing control or HEATR1 shRNA treated with gemcitabine. Cell survival was determined as described in FIG. 1A. The data presented are mean±SD for six independent experiments. ANOVA analysis was performed. +P<0.05, ++P<0.01 (Ctrl vs HEATR1 shRNA #1) *P<0.05, **P<0.01 (Ctrl vs HEATR1 shRNA #2). (B) PANC-1 and ASPC-1 cells were transfected with control or HEATR1 siRNA and then treated with the indicated drugs. Cell survival was determined as described in A. The data presented are mean±SD for six independent experiments. ANOVA analysis was performed. +P<0.05, ++P<0.01 (Ctrl vs HEATR1 KD).

Figure 8:
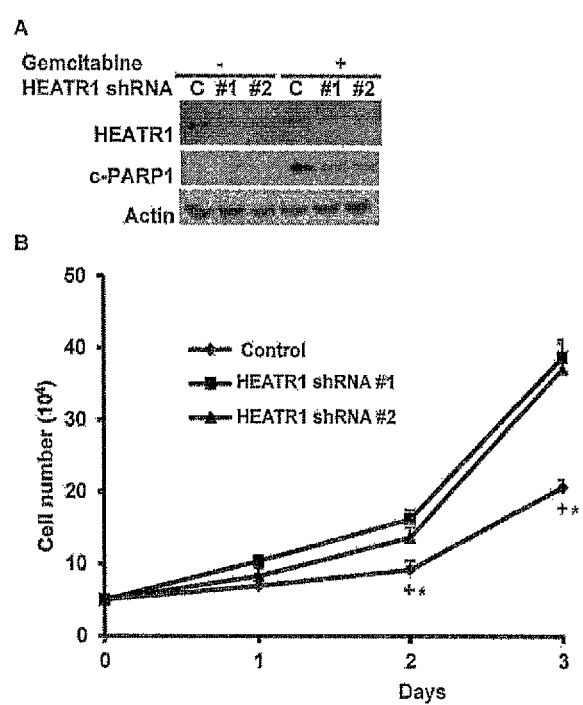

FIG. 8. HEATR1 regulates cancer cell response to chemotherapy and cell growth.

(A) SU86.86 cells stably expressing control or HEATR1 shRNA treated with gemcitabine (10 μM). Cell lysate were collect at 48 hours and western blotting was performed with indicated antibodies. (B) Cells stably expressing control or HEATR1 shRNA were seeded in each well ($5 \times 10^4$/well) and cell numbers were counted every 24 hour. Data are represented as the mean±SD of four independent experiments.

Figure 9:
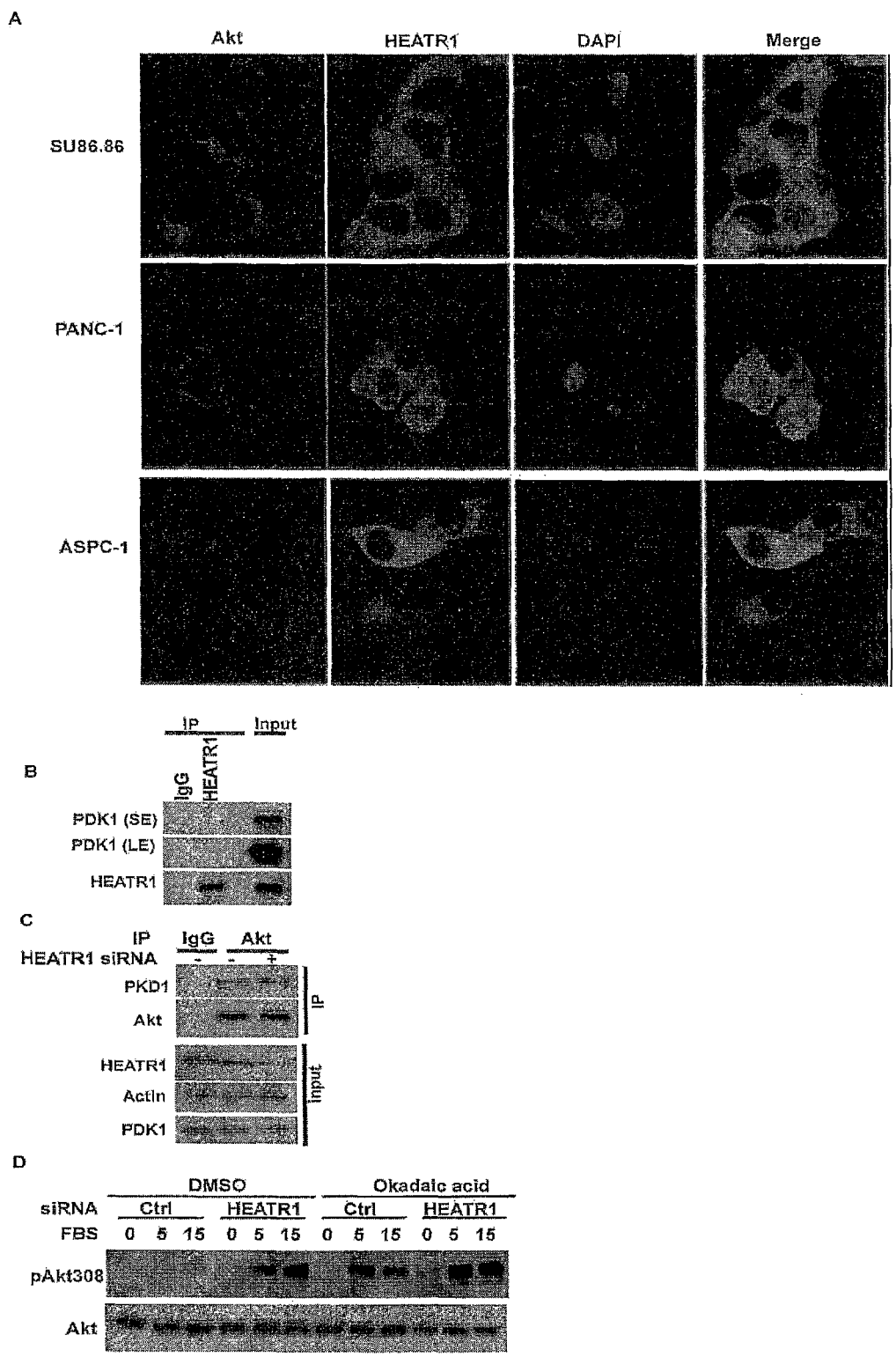

FIG. 9. HEATR1 colocalized with Akt and regulates Akt phosphorylation independent of PDK1.

(A) Intracellular co-localization of HEATR1 and AKT were observed by using confocal microscopy in Su86.86, PANC-1 and ASPC-1 cells. (B) Cell lysates were subjected to immunoprecipitation with control IgG or anti-HEATR1 antibodies. The immunoprecipitates were then blotted with indicated antibodies. (C) Cells were transfected with control or HEATR1 siRNA, and the interaction between Akt and PDK1 was examined. (D) SU86.86 Cells transfected with control or HEATR1 siRNA were serum starved for 16 hours (0.1% serum), pretreated with DMSO or okadaic acid (5 nM) and then serum was added. Whole-cell lysates were harvested at indicated time and western blotting was performed with indicated antibodies.

Figure 10:
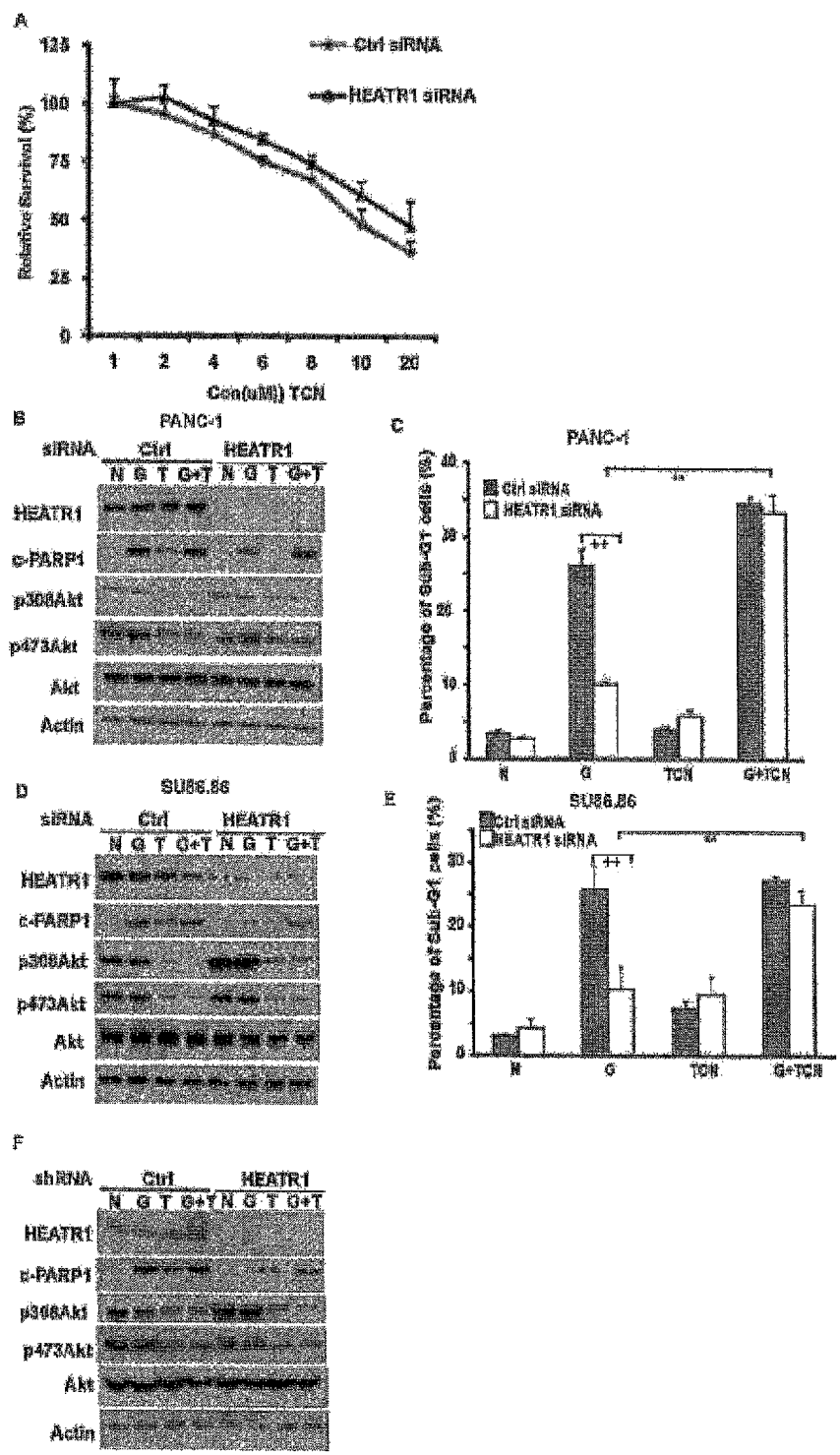

FIG. 10. Akt inhibitor sensitizes pancreatic tumors with HEATR1 knockdown to gemcitabine.

Figure 4:
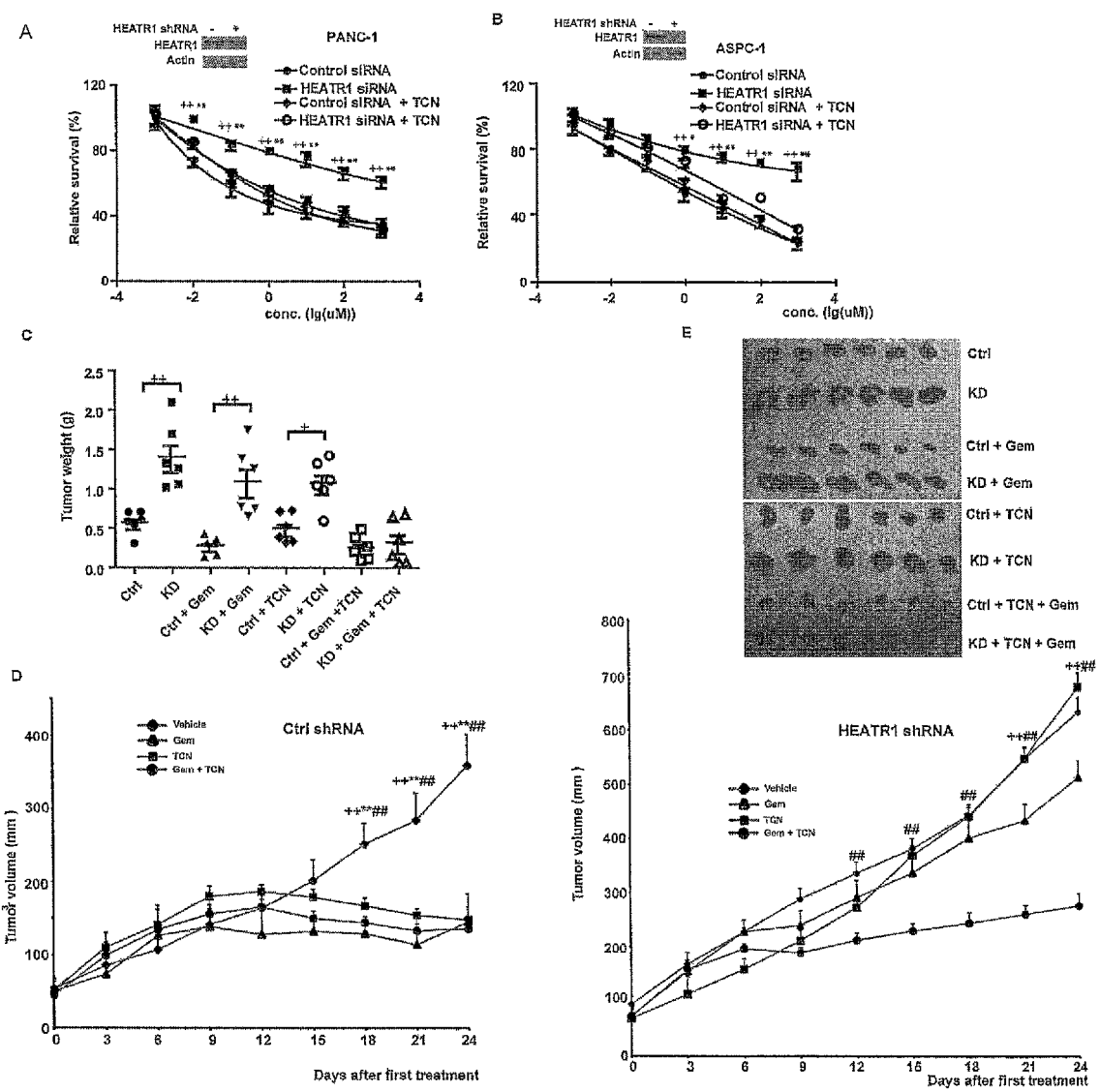
FIG. 4. Akt inhibitor sensitizes pancreatic tumors with HEATR1 knockdown to Gemcitabine. (A-B) PANC-1 (A) or ASPC-1 (B) cells were transfected with indicated siRNA. Gemcitabine sensitivity was examined in the presence of vehicle or 10 μM TCN. Data represent means±SD (n=6). ++P<0.01 (Control vs HEATR1 siRNA), P<0.01 (HEATR1 siRNA vs HEATR1 siRNA+TCN). (C-E) Mice with subcutaneously established tumors from PANC-1 cell stably expressing indicated shRNA were treated with PBS, TCN (0.5 mg/kg), Gemcitabine (50 mg/kg) or combination. Xenograft tumors were dissected and tumor weights were measured after mice were sacrificed (C). ANOVA analysis was performed (Mann-Whitney test) +P<0.05, ++P<0.01 (Ctrl vs KD). Tumor volumes were measured every three days (D). ++P<0.01 (Vehicle vs Gemcitabine), P<0.01 (Vehicle vs TCN) and ##P<0.01 (Vehicle vs Gemcitabine plus TCN). Representative photographs of indicated xenograft tumors were shown in (E).

(A) SU86.86 cells were transfected with control or HEATR1 siRNA and then treated with AKT inhibitor triciribine (TCN). Cell survival was determined as described in the Methods. (B-E) PANC-1 (B-C) and SU86.86 (D-E) cells were transfected with control or HEATR1 siRNA and then treated with vehicle (N), 10 μM gemcitabine (G), 10 μM TCN (T) or gemcitabine plus TCN (G+T). Cell lysate were collect at 48 hours and western blotting was performed with indicated antibodies (B,D). Percentage of Sub-G1 cells were measured by flow cytometry (C,E). ANOVA analysis was performed. ++P<0.01 (Ctrl vs HEATR1 siRNA); **P<0.01 (G vs G+T) (F) Mice with subcutaneously established tumors from PANC-1 cell stably expressing control or HEATR1 shRNA were treated as in FIG. 4C. Xenograft tumors were collected and western blotting was performed with indicated antibodies.

Figure 11:
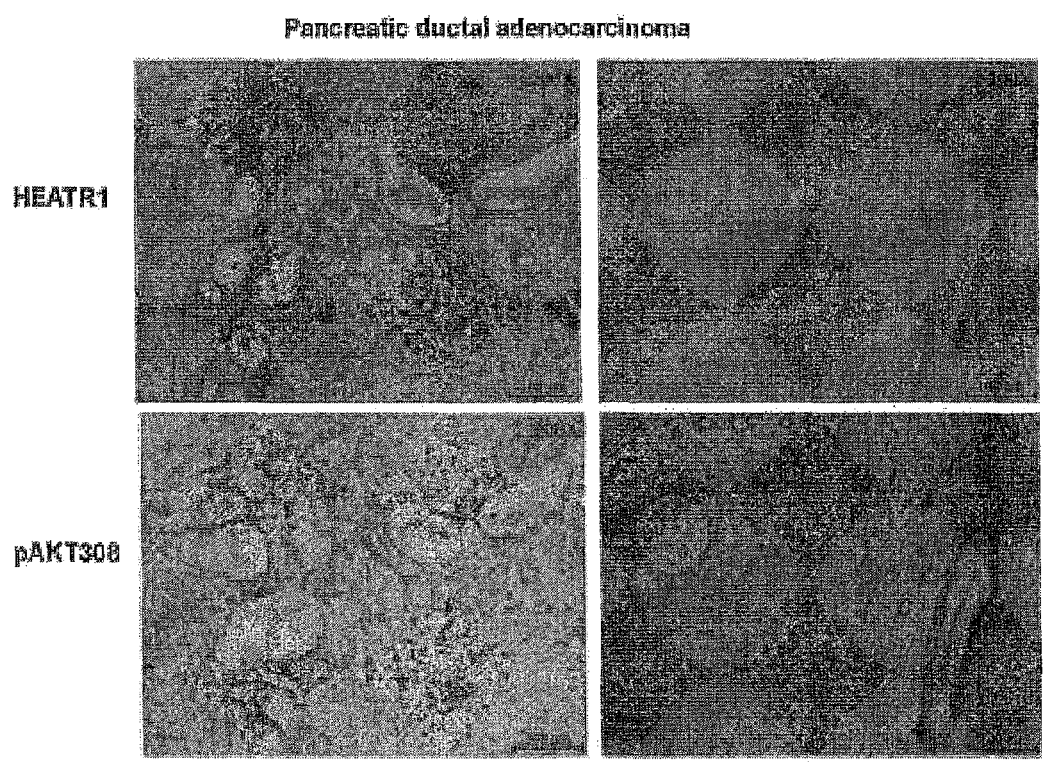

FIG. 11. Representative strong and weak staining of HEATR1 in pancreatic ductal adenocarcinoma. Analysis of HEATR1 staining in pancreatic ductal adenocarcinoma is shown in Table 1.

DEFINITIONS

To facilitate an understanding of the present invention, a number of terms and phrases are defined below. The use of the article "a" or "an" is intended to include one or more. As used herein, terms defined in the singular are intended to include those terms defined in the plural and vice versa.

The term "pancreas" refers to an organ that has exocrine cells, i.e. acinar cells, that make enzymes that help digest the food, along with associated substances forming a pancreatic fluid, and endocrine cells that make hormones for regulating blood glucose levels, i.e. Islets of Langerhans. Enzymes are released from the endocrine cells into tiny tubes called ducts. These exocrine cells release pancreatic fluid into a series of progressively larger tubes (called ducts) that eventually join together to form the main pancreatic duct. The main pancreatic duct runs the length of the pancreas and drains the fluid produced by the exocrine cells into the duodenum, the first part of the small bowel. More than 95% of the cells in the pancreas are exocrine glands and duct cells, i.e. epithelial cells.

The term "pancreatic" is a general term for being 'of' or 'from' the pancreas.

The term "cancer" is intended herein to encompass all forms of abnormal or improperly regulated reproduction of cells in a subject.

The term "primary cancer" refers to cancer cells that arise in the organ or tissue itself, such as pancreas cancer which arises from cells found in the pancreas.

The term "pancreatic cancer" refers to cancer cells that originated from exocrine cells or endocrine cells of the pancreas, each forming different types of tumors (and different types of cancer cells). In other words, "pancreatic cancer" refers to a primary cancer of the pancreas. One example of pancreatic cancer is an exocrine tumor, i.e. Pancreatic adenocarcinoma, a cancer that typically starts in gland cells. However the most common pancreatic tumor is a Pancreatic ductal adenocarcinoma cancer, which typically starts from ductal cells with or without glandular cells.

Cancer of the pancreas is not one disease. In fact, at least twenty different tumors have been lumped under the umbrella term "cancer of the pancreas." Each of these tumors has a different appearance when examined with a microscope, some require different treatments, and each carries its own unique prognosis (predicted or likely outcome). For examples, other cancers of the exocrine pancreas include adenosquamous carcinomas, squamous cell carcinomas, signet ring cell carcinomas, undifferentiated carcinomas, and undifferentiated carcinomas with giant cells. Cancer can develop from the cells that make the pancreatic enzymes, in which case they are called "pancreatic neuroendocrine tumors/carcinomas," or "islet cell tumors/carcinomas."

The term "Pancreatic ductal adenocarcinoma" refers to the vast majority of tumors of the pancreas that typically begins in the exocrine/ductal cells of the pancreas and these cancers look like pancreatic ducts under the microscope. These tumors are therefore called "ductal adenocarcinomas." Are these cancers also called: "adenocarcinoma," or "pancreatic cancer?"

The term "adenocarcinoma" is a general reference to cancer referring to "adeno" meaning 'pertaining to a gland' and "carcinoma" meaning cancer.

The terms "patient" and "subject" refer to a mammal that may be treated using the methods of the present invention. "Subject" and "patient" are used herein interchangeably, and a subject may be any mammal but is preferably a human. A "reference subject" herein refers to an individual who does not have cancer. The "reference subject" thereby provides a basis to which another cell (for example a cancer cell) can be compared.

The term "control" refers to subjects or samples which provide a basis for comparison for experimental subjects or samples. For instance, the use of control subjects or samples permits determinations to be made regarding the efficacy of experimental procedures. In some embodiments, the term "control subject" refers to a subject that which receives a mock treatment (e.g., saline alone).

A "reference subject" or "reference tissue" or "reference cells" as used herein refers to an individual, or tissue or cell that does not have cancer. The "reference" thereby provides a basis to which another cell (for example a cancer cell) can be compared.

The term "tissue sample" refers to both normal tissue, tissue that is suspected of being cancerous, and tissue that is known to be cancerous.

The term "obtaining a tissue sample" in reference to removing a tissue sample, such as a biopsy from a subject, refers to conventional biopsy or surgery techniques. In another example, a blood sample can be removed from the subject, and cells are isolated for use by standard techniques.

The term "diagnose" or "diagnosis", as used herein, refers to the determination, recognition, or identification of the nature, cause, or manifestation of a condition based on signs, symptoms, and/or laboratory findings, such as diagnosing a subject having PDAC.

The term "administering" in reference to a treatment refers to giving a treatment systemically or locally to inhibit tumor cell spread and/or remove cancer cells from cancer patients, including treating cancer cells to inhibit cancer cell division and/or cancer cell growth and/or kill cancer cells, including by inducing apoptotic cell death. Treatments can be administered by a number of routes, including without limitation, intravenously, intrathecally, intraperitoneally, transmucosal, transepithelially, i.e. transdermally, topically, including, for example, patches and iontophoresis devices, as well as topical application of pastes, salves, or ointments, rectally, orally, vaginally, nasally; alone or in combination with, i.e. co-administering a treatment or therapeutic, such as anti-proliferative drugs to reduce the metastatic load in the patient prior to surgery; or administered after surgery.

The term "co-administer", as used herein, refers to a therapy of the administration of two or more agents, drugs, and/or compounds together (i.e. at the same time), such as when administering a combination therapy, for example, administering a chemotherapeutic agent, such as Gemcitabine, and an Akt inhibitor, such as Triciribine.

The term "therapy," used interchangeably herein with "treatment" and variants (e.g., "treating," "administering"), refers to an attempt to prevent or ameliorate a disease ("abnormal condition," "disorder," "syndrome," etc.), such as cancer, or the symptoms thereof, in a patient or a subject. It is not intended that "treating" a disease require curing or eradicating it, such that the treatment may have a therapeutic effect. Therapy can be primary treatment, the first treatment after the initial diagnosis, such as surgery, therapeutics, chemotherapy, radiation, immunotherapy, etc. Therapy can also be treatments after the primary treatment, including follow-up surgery, the same or different therapeutics, chemotherapy, radiation, immunotherapy, etc.

The term "adjuvant therapy", as used herein, refers to additional treatment given after the primary treatment to increase the chances of a cure. In some instances, adjuvant therapy is administered after surgery where all detectable disease has been removed, but where there remains a statistical risk of relapse due to occult disease. If known disease is left behind following surgery, then further treatment is not technically "adjuvant". Adjuvant therapy may include chemotherapy, radiation therapy, hormone therapy, or biological therapy. For example, radiotherapy or chemotherapy is commonly given as adjuvant treatment after surgery for a breast cancer. Oncologists use statistical evidence to assess the risk of disease relapse before deciding on the specific adjuvant therapy. The aim of adjuvant treatment is to improve disease-specific and overall survival. Because the treatment is essentially for a risk, rather than for provable disease, it is accepted that a proportion of patients who receive adjuvant therapy will already have been cured by their primary surgery. Adjuvant chemotherapy and radiotherapy are often given following surgery for many types of cancer, including pancreatic cancer.

The term "changing" in reference to a therapy as in "changing a therapy" refers to such actions such as stopping the administration of one or more current therapeutics, or administering at least one new therapeutic, for example, for a subject receiving Gemcitabine where the cancer cells show low HEATR1 expression, then beginning co-administering an Akt inhibitor, or stopping Gemcitabine, then surgically excising a cancer tissue, or stopping Gemcitabine then co-administering another chemotherapeutic with or without an Akt inhibitor, or beginning administration or co-administration of an AKT inhibitor for inhibiting pAktThr308, such as TCN.

The "therapeutic agent" or a "chemotherapeutic agent" refers to any agent that is intended to confer a desired therapeutic effect on a subject.

The term "therapeutic effect" of a therapy includes the prevention of: recurrence spread of cancer or a reduction in the severity of cancer or a delay in the progression of cancer. It is not intended that the present invention be limited to complete prevention. Similarly, the progression of a disease is considered herein to be "reduced" or "inhibited" if, in the judgment of a practitioner of the healing arts, one or more of the characteristic indicia of progression of the disease are reduced or inhibited.

The term "altering" and grammatical equivalents as used herein in reference to the level of any substance and/or phenomenon refers to an increase and/or decrease in the quantity of the substance and/or phenomenon, regardless of whether the quantity is determined objectively, and/or subjectively.

The terms "under-express", "under-expressing" and grammatical equivalents, as used herein, refer to the production of a gene product in a cancer cell at levels that under production in normal or control cells. The term "under-expression" or "lower expression" may be specifically used in reference to levels of mRNA to indicate a lower level of expression than that typically observed in a given tissue in a control or reference. Levels of mRNA are measured, as in "measuring the level of HEATR1 expression" or "measuring the level of the serine/threonine protein kinase (Akt)" using any of a number of techniques known to those skilled in the art including, but not limited to Northern blot analysis. Appropriate controls are included on the Northern blot to control for differences in the amount of RNA loaded from each tissue analyzed, the amount of 28S rRNA (an abundant RNA transcript present at essentially the same amount in mammalian tissues) present in each sample can be used as a means of normalizing or standardizing the mRNA-specific signal observed on Northern blots. Under-expression may likewise result in elevated levels of proteins encoded by said mRNAs. Another example of an assay for "measuring the level of HEATR1 expression" is using Western blots. Similarly, "measuring the level of" phosphorylated Akt 308 (Akt308) is by using Western blots, with or without radiolabeled pAkt.

The terms "reduce," "inhibit," "diminish," "suppress," "decrease," and grammatical equivalents when used in reference to the level of a substance and/or phenomenon in a first sample relative to a second sample, mean that the quantity of substance and/or phenomenon in the first sample is lower than in the second sample by any amount that is statistically significant using any art-accepted statistical method of analysis. As one example, an Akt inhibitor reduces the activity of the Akt protein, such as reducing phosphorylation of Akt (i.e. reducing pAkt), where in preferred embodiments, phosphorylation of pThr308 is reduced. In another embodiment, the quantity of substance and/or phenomenon in the first sample is at least 10% lower than the quantity of the same substance and/or phenomenon in a second sample. In another embodiment, the quantity of the substance and/or phenomenon in the first sample is at least 25% lower than the quantity of the same substance and/or phenomenon in a second sample. In yet another embodiment, the quantity of the substance and/or phenomenon in the first sample is at least 50% lower than the quantity of the same substance and/or phenomenon in a second sample. In a further embodiment, the quantity of the substance and/or phenomenon in the first sample is at least 75% lower than the quantity of the same substance and/or phenomenon in a second sample. In yet another embodiment, the quantity of the substance and/or phenomenon in the first sample is at least 90% lower than the quantity of the same substance and/or phenomenon in a second sample. Alternatively, a difference may be expressed as an "n-fold" difference. Relative to a subject, before, during or after therapy, a reduction of cancer may be determined subjectively, for example when a patient refers to their subjective perception of a reduction in disease symptoms, such as pain, etc., or by a medical person using a diagnostic test to measure a decrease in cancer.

The terms "phosphorylation" refers to the addition of a phosphate ($PO_4^{3-}$) group to a protein or other organic molecule, such as Akt (threonine 308 (Thr308) and/or serine 473 (Ser473)) or specifically Akt Thr308 or Ser473.

The terms "over-express", "over-expressing" and grammatical equivalents, as used herein, refer to the production of a gene product in a cancer cell at levels that exceed production in normal or control cells. The term "over-expression" or "highly expressed" may be specifically used in reference to levels of mRNA to indicate a higher level of expression in a cancer cell or tissue than that typically observed in a given tissue in a control or reference. Levels of mRNA are measured, as in "measuring the level of HEATR1 expression" or "measuring the level of the serine/threonine protein kinase (Akt)" using any of a number of techniques known to those skilled in the art including, but not limited to Northern blot analysis. Appropriate controls are included on the Northern blot to control for differences in the amount of RNA loaded from each tissue analyzed, the amount of 28S rRNA (an abundant RNA transcript present at essentially the same amount in mammalian tissues) present in each sample can be used as a means of normalizing or standardizing the mRNA-specific signal observed on Northern blots. Over-expression may likewise result in elevated levels of proteins encoded by said mRNAs. Another example of an assay for "measuring the level of HEATR1 expression" is using Western blots or immunohistochemistry (IHC). Similarly, "measuring the level of" phosphorylated Akt 308 (Akt308) is by using Western blots or IHC, with or without radiolabeled pAkt.

The terms "increase," "elevate," "raise," and grammatical equivalents when used in reference to the level of a substance and/or phenomenon in a first sample relative to a second sample, mean that the quantity of the substance and/or phenomenon in the first sample is higher than in the second sample by any amount that is statistically significant using any art-accepted statistical method of analysis. In one embodiment, the quantity of the substance and/or phenomenon in the first sample is at least 10% greater than the quantity of the same substance and/or phenomenon in a second sample. In another embodiment, the quantity of the substance and/or phenomenon in the first sample is at least 25% greater than the quantity of the same substance and/or phenomenon in a second sample. In yet another embodiment, the quantity of the substance and/or phenomenon in the first sample is at least 50% greater than the quantity of the same substance and/or phenomenon in a second sample. In a further embodiment, the quantity of the substance and/or phenomenon in the first sample is at least 75% greater than the quantity of the same substance and/or phenomenon in a second sample. In yet another embodiment, the quantity of the substance and/or phenomenon in the first sample is at least 90% greater than the quantity of the same substance and/or phenomenon in a second sample. Alternatively, a difference may be expressed as an "n-fold" difference. Relative to a subject, before, during or after therapy, a reduction of cancer may be determined subjectively, for example when a patient refers to their subjective perception of an increase in disease symptoms, such as pain, etc., or by a medical person using a diagnostic test to measure an increase in cancer.

The term "resistance", as used herein, refers to cancer cells or subjects that do not respond to chemotherapy drugs (i.e. chemotherapeutic agents). Typically, a first course of chemotherapy may prove highly beneficial, nearly annihilating a tumor, but a few resistant cancer cells often survive and proliferate. Too often, despite more aggressive second and third courses of chemotherapy, the remaining drug-defiant cells thrive, displaying increasing resistance to drug therapy and eventually displaying virtual invulnerability to chemotherapy. After the drug's effectiveness fades, the patient relapses. This occurs in patients with a variety of blood cancers and solid tumors, including breast, ovarian, lung, and lower gastrointestinal tract cancers. Nature Biotechnology 18:IT18-IT20 (2000). Resistance to treatment with anticancer drugs results from a variety of factors including individual variations in patients and somatic cell genetic differences in tumors, even those from the same tissue of origin. Frequently resistance is intrinsic to the cancer, but as therapy becomes more and more effective, acquired resistance has also become common. The development of multidrug resistance (MDR) to chemotherapy remains a major challenge in the treatment of cancer. Resistance exists against every effective anticancer drug and can develop by numerous mechanisms including decreased drug uptake, increased drug efflux, activation of detoxifying systems, activation of DNA repair mechanisms, and insensitivity to drug-induced apoptosis. Methods Mol. Biol. 596: 47-76 (2010). Thus, in some embodiments, the present invention contemplates treating drug resistant cancer cells. It is not intended that the present invention be limited to the degree of resistance, i.e. resistance can be shown simply by the fact that it takes higher doses of drug to kill these cells. The cells need not be resistant at every dose. The cells may be resistant such that higher doses needed to kill the cells will not be well tolerated by the patient.

The term "apoptosis", as used herein, refers to a form of programmed cell death in cells of multicellular organisms that involves a series of biochemical events that lead to a variety of morphological changes, including cell surface blebbing, changes to the cell membrane such as loss of membrane asymmetry and attachment, cell shrinkage, nuclear fragmentation, chromatin condensation, and chromosomal DNA fragmentation. Defective apoptotic processes have been implicated in an extensive variety of diseases; for example, defects in the apoptotic pathway conferring resistance to compounds that typically induce apoptotic cell death have been implicated in diseases associated with uncontrolled cell proliferations, such as cancer. In some embodiments, killing a cancer cell refers to inducing apoptosis in a cancer cell.

The term "wild type" refers to a gene or gene product or level of expression that has the characteristics of that gene or gene product or level of expression when isolated or measured from/in a naturally occurring source. A wild type gene is the variant most frequently observed in a population and is thus arbitrarily designed the "normal" or "wild-type" form of the gene. Similarly, a "normal" expression level is a relative amount of mRNA or protein when measured from noncancerous cells or noncancerous tissues.

The term "knockdown", as used herein, refers to a method of selectively preventing the expression of a gene in an individual.

As used herein, the term "shRNA" or "short hairpin RNA" refers to a sequence of ribonucleotides comprising a single-stranded RNA polymer that makes a tight hairpin turn on itself to provide a "double-stranded" or duplexed region. shRNA can be used to silence gene expression via RNA interference. shRNA hairpin is cleaved into short interfering RNAs (siRNA) by the cellular machinery and then bound to the RNA-induced silencing complex (RISC). It is believed that the complex inhibits RNA as a consequence of the complexed siRNA hybridizing to and cleaving RNAs that match the siRNA that is bound thereto.

As used herein, the term "RNA interference" or "RNAi" refers to the silencing or decreasing of gene expression by siRNAs. It is the process of sequence-specific, posttranscriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi inhibits the gene by compromising the function of a target RNA, completely or partially. Both plants and animals mediate RNAi by the RNA-induced silencing complex (RISC); a sequence-specific, multicomponent nuclease that destroys messenger RNAs homologous to the silencing trigger. RISC is known to contain short RNAs (approximately 22 nucleotides) derived from the double-stranded RNA trigger, although the protein components of this activity are unknown. However, the 22-nucleotide RNA sequences are homologous to the target gene that is being suppressed. Thus, the 22-nucleotide sequences appear to serve as guide sequences to instruct a multicomponent nuclease, RISC, to destroy the specific mRNAs. Carthew reported (Curr. Opin. Cell Biol. 13(2): 244-248 (2001)) that eukaryotes silence gene expression in the presence of dsRNA homologous to the silenced gene. Biochemical reactions that recapitulate this phenomenon generate RNA fragments of 21 to 23 nucleotides from the double-stranded RNA. These stably associate with an RNA endonuclease, and probably serve as a discriminator to select mRNAs. Once selected, mRNAs are cleaved at sites 21 to 23 nucleotides apart.

As used herein, the term "siRNAs" refers to short interfering RNAs. In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to or substantially complementary to a target RNA molecule. The strand complementary to a target RNA molecule is the "antisense strand"; the strand homologous to the target RNA molecule is the "sense strand", and is also complementary to the siRNA antisense strand. siRNAs may also contain additional sequences; non-limiting examples of such sequences include linking sequences, or loops, as well as stem and other folded structures. siRNAs appear to function as intermediaries in triggering RNA interference in invertebrates and in vertebrates, and in triggering sequence-specific RNA degradation during posttranscriptional gene silencing in plants.

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (Sambrook, et al., supra, pp. 7.39-7.52, 1989).

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabelled antibodies.

DESCRIPTION OF THE INVENTION

The present invention relates to methods of using HEATR1 expression levels for guiding chemotherapy treatment of pancreatic cancer. In particular, measuring lower HEATR1 expression in pancreatic cancer is associated with resistance to the use of certain chemotherapy treatments such that by changing the treatment a better prognosis may be obtained for the patient. Further, lower HEATR1 expression is related to a poorer long-term prognosis of pancreatic cancer patients thus measuring an increase or maintenance/decrease during treatment may be useful for predicting treatment response.

Overcoming chemoresistance is needed for cancer therapy, in particular pancreatic cancer such as pancreatic ductal adenocarcinoma (PDAC). The inventors' genome wide association studies (GWAS) showed that HEATR1 gene is associated with cellular sensitivity AraC resistance. Further discoveries during the development of the present inventions by experimental studies showed that depletion of HEATR1 by its specific siRNA causes resistance to oxaliplatin, mitomycin C, SN-38, etoposide Camptothecin and paclitaxel in several pancreatic cancer cell lines.

Diagnostic and prognostic biomarkers for PADC patients are known (29). However, existing biomarkers such as CA19-9 are not adequate as early detection markers of pancreatic cancer and predictor to treatment response because of low sensitivity and specificity (37).

The inventors' subsequently found that expression level of HEATR1 was significantly downregulated in pancreatic ductal adenocarcinoma (PDAC), which correlated with increase of Akt phosphorylation, short survival and poor response to radical resection plus standardized Gemcitabine chemotherapy in PDAC patients. In contrast, the inventors found that pateints with higher HEATR1 expression is sensitive to monotherapy of gemcitabine, and combination therapy with Akt inhibitor is not necessary.

Moreover, HEATR1 was found to enhance Gemcitabine response by acting as a scaffolding protein for Akt and PP2A and promoting dephosphorylation of AktThr308. Treating cells with the Akt inhibitor TCN sensitized HEATR1 depleted pancreatic cancer cells to Gemcitabine both in vitro and in vivo, suggesting that combination therapy of Gemcitabine and Akt inhibitor would overcome Gemcitabine resistance in patients with low HEATR1 expression. Therefore, HEATR1 is a Akt regulator and is contemplated to be a useful for determining prognosis and as a response predictor for PDAC patients.

HEAT Repeat-Containing Protein 1 (HEATR1).

HEAT repeat-containing protein 1 (HEATR1; UTP10; protein BAP28) refers to a gene, its mRNA or its encoded protein, containing HEAT repeats, which was initially found in a diverse family of proteins including Huntingtin, Elongation factor-3, the PR65/A subunit of protein phosphatase 2A (22) and the yeast PI3-kinase TOR1. HEAT repeats correspond to tandemly arranged curlicue-like structures of about a 37-47 amino acid repeated region, that appear to serve as flexible scaffolding on which other components can assemble. Neuwald and Hirano, "HEAT Repeats Associated with Condensins, Cohesins, and Other Complexes Involved in Chromosome-Related Functions." Genome Res. 2000 October; 10(10): 1445-1452. Published reports suggest that HEATR1 may regulate rRNA synthesis and cytotoxic T lymphocytes in patients with glioma (23, 24).

HEATR1 as a Potential Prognostic Marker of Pancreatic Cancers.

HEATR1 expression is loosely associated with cancer, including pancreatic cancer, and further associated with resistance to chemotherapeutic agents in several publications. However none of the exemplary references described below provide specific instructions or methods of measuring lower HEART1 levels in pancreatic ductal adenocarcinoma cancer specifically for guidance in prescribing or changing a specific treatment. In fact, there is no teaching of using HEART1 expression for selecting subjects for alternative therapy. Thus, in one embodiment, measuring lower HEART1 levels in pancreatic ductal adenocarcinoma cancer compared to noncancerous cells/tissues (i.e. noncancerous samples) is contemplated to guide a healthcare practitioner to choose a therapy for the patient. In one embodiment, measuring lower HEART1 levels in pancreatic ductal adenocarcinoma cancer compared to noncancerous cells/tissues (i.e. noncancerous samples) is contemplated to guide a healthcare practitioner to administer a particular therapy to a patient. In one embodiment, measuring lower HEART1 levels in pancreatic ductal adenocarcinoma cancer compared to noncancerous cells/tissues (i.e. noncancerous samples) is contemplated to guide a healthcare practitioner to change the treatment of the patient. In one embodiment, measuring lower HEART1 levels in pancreatic ductal adenocarcinoma cancer compared to noncancerous cells/tissues (i.e. noncancerous samples) is contemplated to guide a healthcare practitioner to administer a new treatment to the patient.

Further, these references do not describe measuring HEATR1 expression then using the results for guidance on initiating a therapy with a named therapeutic and/or for use in guiding or changing a therapy. Additionally, some chemotherapeutics themselves were found to lower expression of HEART1. Thus, in one embodiment, measuring lower HEART1 levels in pancreatic ductal adenocarcinoma cancer of a patient undergoing a therapy compared to pancreatic ductal adenocarcinoma cancer cells/tissues prior to onset of a therapy is contemplated to guide a healthcare practitioner to change the treatment of the subject.

The following are several references that mention HEART1 as biomarkers in cancer, including pancreatic cancer, with their noted deficiencies. WO2012142330. "Micro RNAs As Diagnostic Biomarkers And Therapeutics For Ovarian Cancer And Metastatic Tumors That Disseminate Within The Peritoneal Cavity." Published Dec. 4, 2012, where HEATR1 is listed as one of 500 downregulated biomarkers indicating resistance to a chemotherapeutic agent. Although pancreatic cancer was mentioned, there is no specific statement that pancreatic cancer has downregulated HEATR1 and there is no name of a chemotherapeutic agent in relation to HEATR1 or pancreatic cancer. WO 2013098797. "Diagnostic tests for predicting prognosis, recurrence, resistance or sensitivity to therapy and metastatic status in cancer." Published Jul. 4, 2013, describes methods relating to lists of genes for use in diagnostic tests for predicting prognosis and response to cancer therapy. Cancer types are head and neck tumors in general, including tongue cancer, where pancreatic cancer was mentioned in association with HEATR1, as one of numerous listed genes, for predicting resistance to chemotherapy. However there is no indication of what specific characteristic of the HEATR1 gene associates with pancreatic cancer or with which named chemotherapeutic; WO2014151117. "Identification And Use Of Circulating Nucleic Acid Tumor Markers." Published Sep. 25, 2014, describes a method of using cell free DNA and tumor tissue DNA, where at least one gene has a mutation, for therapy selection for a cancer subject. HEATR1 is listed as a tumor marker without instructions on to how to use it. Although pancreatic cancer is associated with a list of selector genes, HEATR1 is not on this list; WO 2015063302, "Personalized immunotherapy against several neuronal and brain tumors." Published May 7, 2015, where a peptide of human HEAT repeat containing 1 (HEATR1) was described for stimulating anti-tumor immune responses associated with overexpression of that peptide in a particular tumor type because overexpression indicated poor survival. Although biomarkers for pancreas cancer were named, HEATR1 was not on this list. For prostate cancer, HEATR1 is listed as a gene for predicting prostate cancer fast relapse using prostate cancer tissues. However, there is no specific characteristic of HEATR1 associated with cancer tissues or a recommendation of therapy related to HEATR1 or indication of how HEATR1 specifically is used to predict relapse: US 20130079241. "Methods for Diagnosing Prostate Cancer and Predicting Prostate Cancer Relapse." Published 28 Mar. 2013.

Surprisingly HEATR1 is a Prognostic Biomarker of Pancreatic Cancers.

In contrast to the references described herein, during the development of the present inventions HEATR1 expression levels were discovered to regulate pancreatic cancer cell response to multiple classes of named chemotherapeutic drugs. Changes in expression levels of the HEATR1 gene are shown here, i.e. artificially suppressed, were associated with reduced sensitivity to specific types of chemotherapy. As another example, expression levels of HEATR1 were significantly downregulated in pancreatic ductal adenocarcinoma (PDAC), which correlated with increased Akt phosphorylation, short survival and poor response to radical resection plus standardized Gemcitabine chemotherapy in PDAC patients. Thus HEATR1 is contemplated as a prognostic marker of pancreatic cancers.

Figure 1:
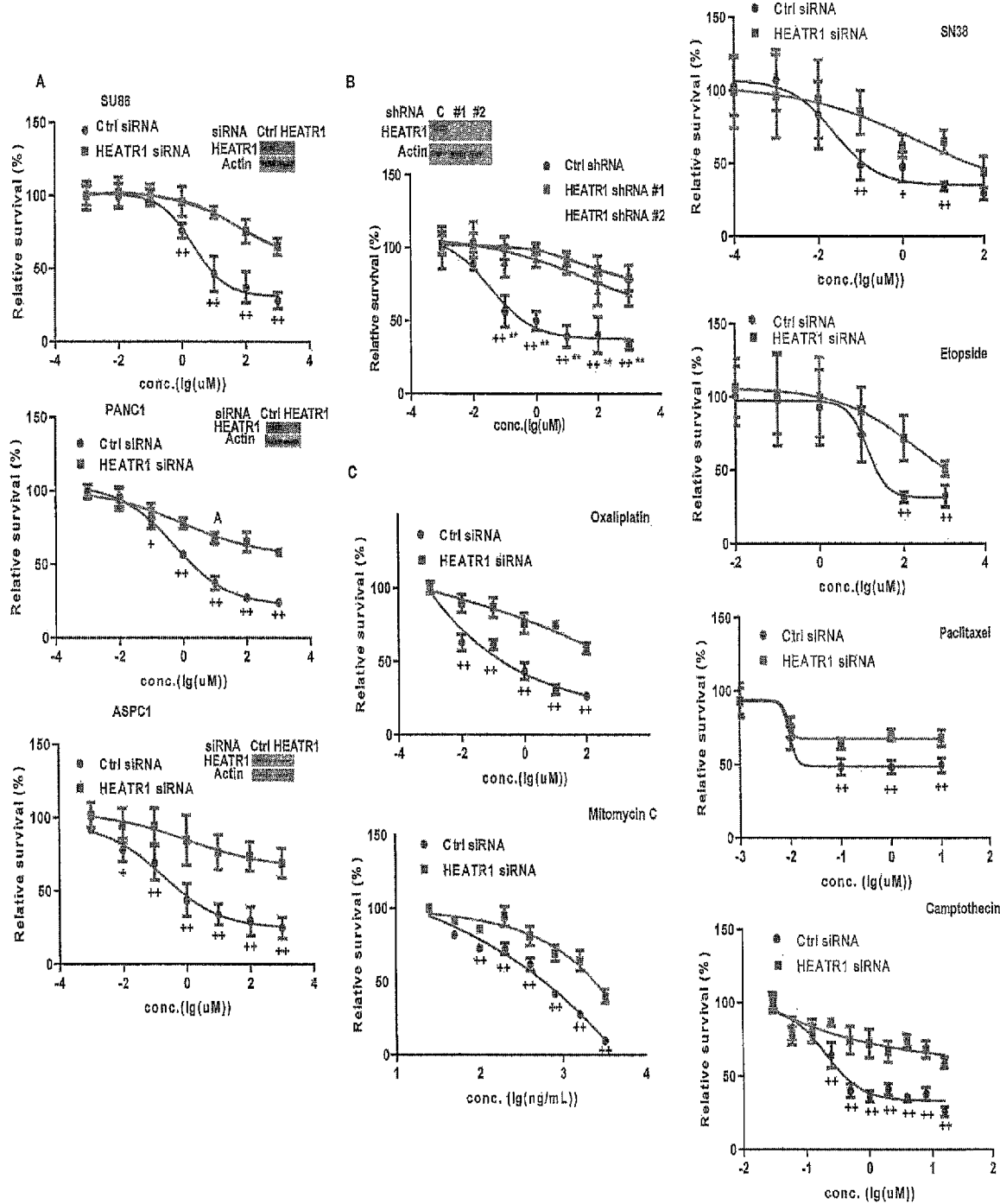
FIG. 1. HEATR1 regulates cancer cell response to chemotherapy. (A) Cells were transfected with indicated siRNA and treated with Gemcitabine. Cell survival was determined. The data presented are mean±SD (n=6). +$P<0.05$, ++$P<0.01$ (Ctrl vs HEATR1 siRNA) (B) SU86.86 cells stably expressing indicated shRNA were treated with Gemcitabine. Cell survival was determined. +*$P<0.05$, ++**$P<0.01$ (Ctrl vs HEATR1 shRNA #1 or #2 respectively). (C) SU86.86 cells were transfected with indicated siRNA and treated. Cell survival was determined.
Figure 2:
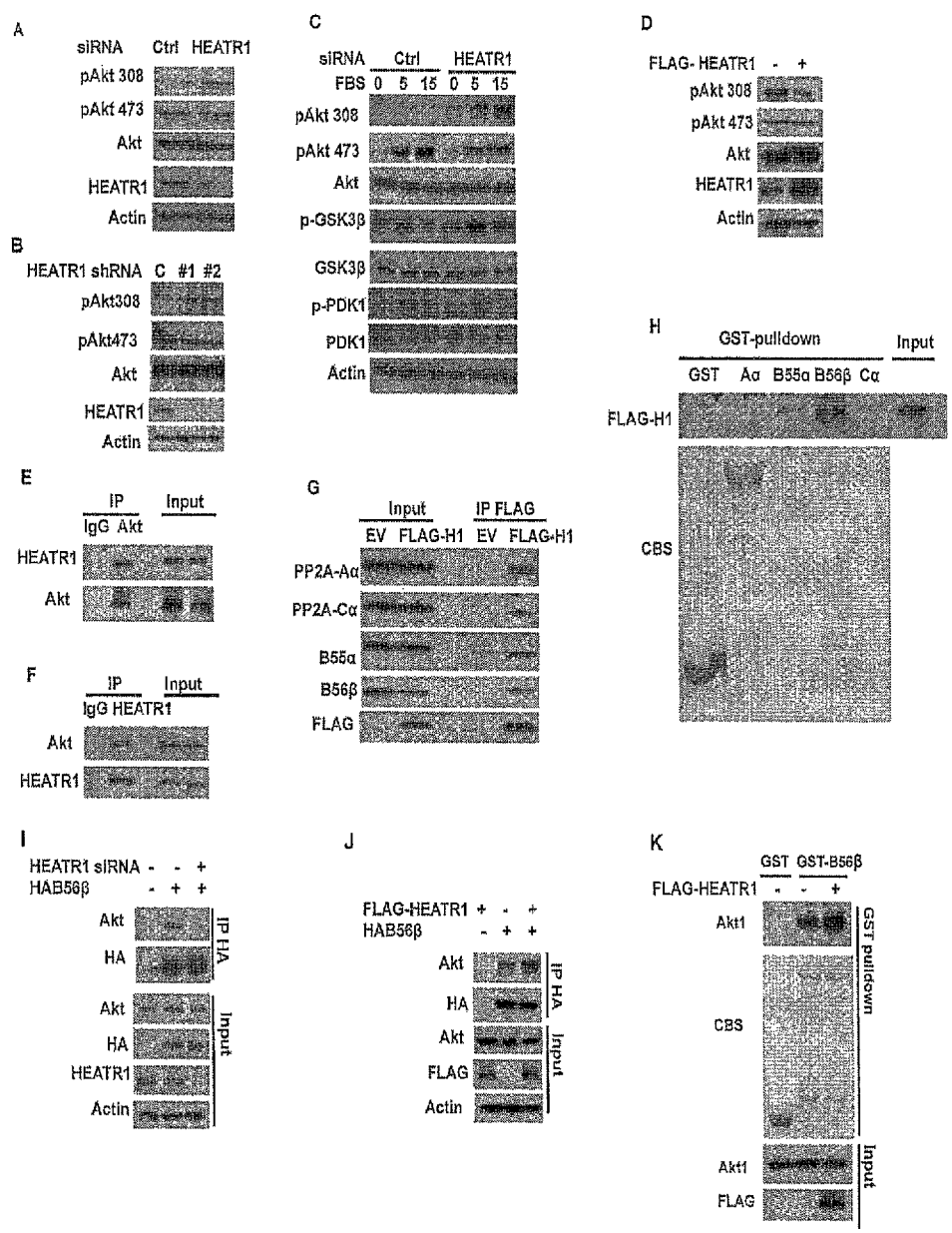
FIG. 2. HEATR1 regulates Akt phosphorylation at Thr308 by promoting Akt-B56β interaction. (A) Cells were transfected with indicated siRNA; the phosphorylation of Akt was detected. (B) Cells were transfected with indicated shRNA and the phosphorylation of Akt was detected. (C) Cells transfected with indicated siRNA were serum starved for 16 hours and then serum was added. Whole-cell lysates were harvested and western blotting was performed. (D) Cells were transfected with indicated constructs and Akt phosphorylation were detected. (E-F) Cell lysates were subjected to immunoprecipitation with control IgG, anti-Akt (E) or anti-HEATR1 (F) antibodies. The immunoprecipitates were blotted with indicated antibodies. (G) Cells were transfected with vector or FLAG-HEATR1 and immunoprecipitated with anti-FLAG beads, followed by western analysis. (H) Cells were transfected with FLAG-HEATR1. Immunoprecipitates with anti-FLAG beads were washed extensively and eluted with FLAG peptide. Elutes were incubated indicated GST or GST-fusion protein and western blotting were performed. (I) Cells were transfected with control or HEATR1 siRNA, then the interaction between Akt and B56β was examined. (J) Cells were transfected with indicated constructs then the interaction between Akt and B56β was examined. (K) Purified recombinant Akt, GST-B56β and FLAG-HEATR1 were incubated in vitro as indicated. The interaction between Akt and B56β was then examined.
Figure 3:
FIG. 3. HEATR1 scaffolding function regulated Akt phosphorylation and cell survival. (A) Schematic diagram of WT and deletion mutants of HEATR1 used in the study. (B-C) Cells were transfected with indicated constructs. Precipitation reactions were conducted with S-protein agarose beads and subjected to western blotting. (D) Cells were transfected with indicated constructs. Western blotting was performed. (E) Cells were transfected as in (D) and Gemcitabine sensitivity was examined. The data presented are mean±SD (n=6). +P<0.05, ++P<0.01 (Ctrl vs HEATR1 KD-knockdown)
Figure 3:
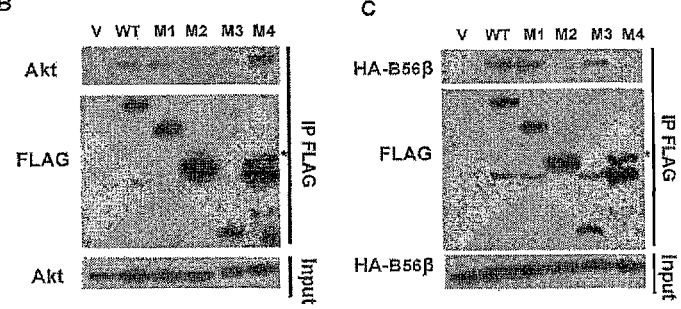
Figure 3:
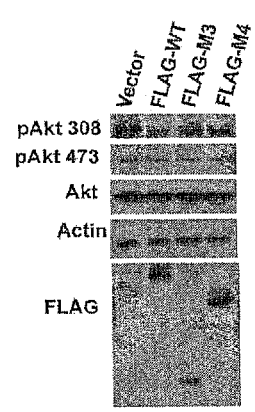
Figure 3:
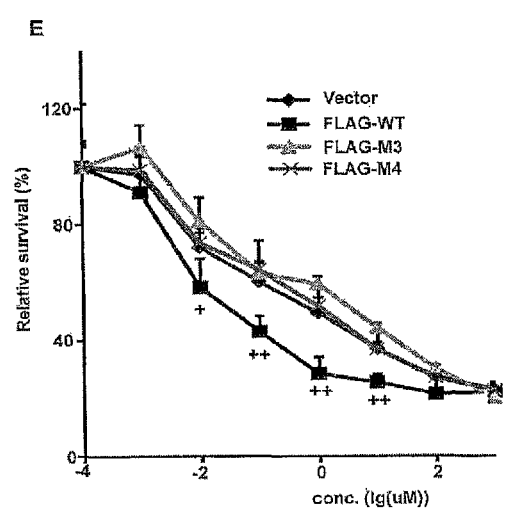
Figure 5:
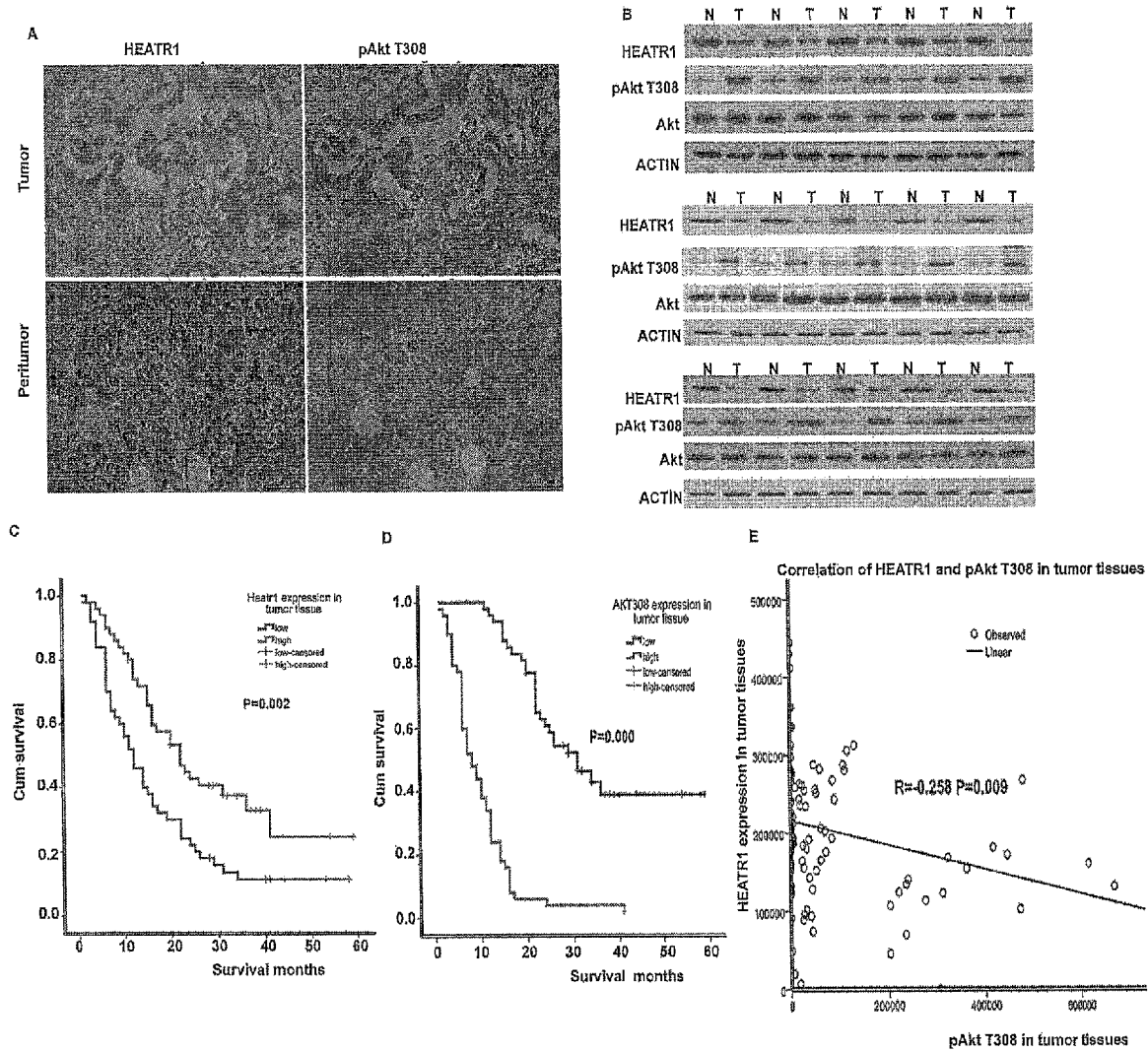
FIG. 5. Association of HEATR1 expressions in pancreatic cancer patients with survival and response to chemotherapy. (A) Representative staining of HEATR1 and pAkt T308 in peritumoral pancreatic tissues and pancreatic ductal adenocarcinoma. (B) Western blot of lysates from a subset of tumor and normal tissues. (C-D) Univariate survival of HEATR1 and pAkt T308. (E) Correlation of expression of HEATR1 and pAkt T308 in tumor tissues. (F) Three levels of HEATR1 expression related to long-term survival. Patients having strong HEATR1 expression were more likely to live longer than patients with weaker expression.
Figure 7:
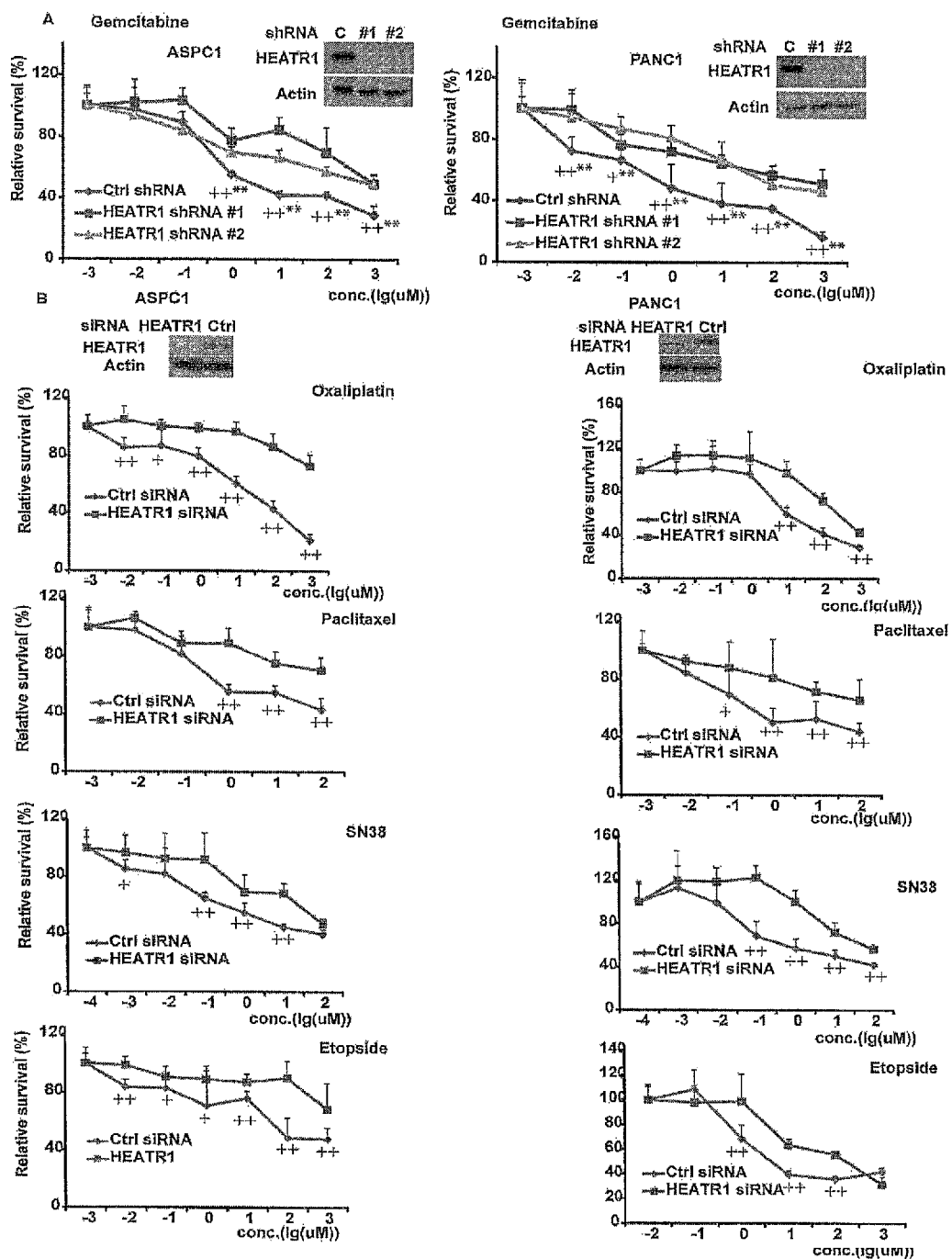
FIG. 7. HEATR1 regulates cancer cell response to chemotherapy.

Specifically, depletion of HEATR1 in pancreatic cancer cells, in particular by siRNA silencing of HEATR1 expression, was shown to cause resistance to Gemcitabine and other chemotherapeutic agents (FIG. 1 and FIG. 7). Thus, HEATR1 functions in Gemcitabine resistance through inhibiting Akt activity as demonstrated by the following experiments. First, the interaction between Akt and B56β was decreased when HEATR1 was depleted, indicating that HEATR1 acts as a scaffolding protein for Akt and B56β, thereby enhancing the phosphatase activity of B56β toward Thr308 (FIG. 2). Second, HEATR1 mutants that abolish Akt or B56β interaction failed to affect Akt Thr308 phosphorylation and chemosensitity (FIG. 3). Third, addition of triciribine (TCN) sensitizes Gemcitabine treatment in cells with low HEATR1 level both in vitro (FIG. 4A) and in animal models (FIG. 3B-D). In fact, expression of HEATR1 in PDAC pateints is positively correlated with overall survival in patients with pancreatic cancer (see, FIG. 5). For example, the group of patients having the lowest expression levels had the hightes death rate, the highest expression levels correlated with a higher survival rate. The intermediate group showed a survival rate in between the low and high expressors. Thus, in one embodiment, HEATR1 expression levels are a prognostic marker for surviving pancreatic cancer, (see, FIG. 5F).

Using HEATR1 as a Prognostic Biomarker for Guidance in Treating Pancreatic Cancers.

Thus, the inventors contemplate embodiments of the present inventions using HEATR1 as a biomarker for making treatment decisions for PDAC patients. Therapeutic interventions using HEATR1 as a biomarker is contemplated to improve patient outcome in combination with existing therapies. Because Gemcitabine represents the standard of care for PDAC yet does not improve numerous patients with PDAC, the inventors' contemplate using HEATR1 expression levels for making decisions related to Gemcitabine treatment in combination with a HEATR1 substrate, i.e. Akt inhibitor whose activity increases as HEATR1 activity decreases. Thus, in one embodiment, measuring lower HEART1 levels in pancreatic ductal adenocarcinoma cancer compared to noncancerous cells/tissues (i.e. noncancerous samples) is contemplated to guide a healthcare practitioner to administer a combination therapy of an Akt inhibitor and a chemotherapeutic. In another embodiment, measuring lower HEATR1 expression levels, in particular for patients undergoing therapy, indicates unsuccessful treatment of the patient that is information for use in guiding a health practitioner to change therapy for a more successful treatment, for example, with the goal of stopping or reversing cancer progression, reducing undesireable symptoms, reducing pain, and ideally extending the life of the patient. Thus, in one embodiment, measuring lower HEART1 levels in pancreatic ductal adenocarcinoma cancer compared to cancerous cells/tissues (i.e. during a primary treatment is contemplated to guide a healthcare practitioner to administer a combination therapy of an Akt inhibitor and a chemotherapeutic that is not the same named compounds of the primary treatment.

The results from animal experiments during the development of the present invention demonstrated that by using HEATR1 expression levels to guide treatment there is better success in treatment outcome.

Contemplative Treatments Based Upon Regulation of HEART1 Expression.

Several genome wide association studies were performed by others to identify genes whose expression associates with sensitivity to chemotherapy. (See, 26 as an example). Surprisingly, the HEATR1 gene was not among the top hits in these studies therefore it was not identified as relevant to responses to chemotherapeutic drugs including Gemcitabine and 1-beta-d-arabinofuranosylcytosine. In contrast, the inventors showed that HEATR1 expression levels associated with responses to several drugs, including Gemcitabine and 1-beta-d-arabinofuranosylcytosine.

HEATR1 was then depleted during the development of the present inventions with siRNA in cells and treated cells with Gemcitabine. Downregulation of HEATR1 resulted in increased resistance to Gemcitabine (FIG. 1A). Similar results were obtained with two HEATR1 specific shRNAs (FIG. 1B and FIG. 7A). Next, multiple classes of chemotherapeutic drugs including oxaliplatin, SN-38, mitomycin c (MMC), paclitaxel, Camptothecin and etopside were used to treat cells. Similarly, cells with HEATR1 knockdown were significantly resistant to these drugs (FIG. 1C and FIG. 7B). These results establish a role of HEATR1 in regulating chemo-response to different anti-tumor agents.

HEATR1 contains 2144 amino acids, thus making it difficult to contemplate methods of restoring expression using the entire protein molecule of HEATR1 in PADC cancer cells. Thus, the inventors contemplate identifying small/short motifs of HEATR1 responsible Akt or PP2A binding, in order to engineer a polypeptide to restore the regulation of Akt by PP2A. Further, by identifying the mechanism of HEATR1 downregulation in PDAC, such as decreased translation or increase in protein turnover, this information might be used to restore HEATR1 expression.

However, after searching public databases (TCGA and Oncomine), HEATR1 mRNA was not reported as downregulated in PDAC. Moreover, the inventors found that the HEATR1 gene is mutated in a small percentage of pancreatic cancer cases (3.4% TCGA). Yet, this does not account for the percentage of pancreatic cancers showing at least weak HEATR1 immunohistochemistry staining. Therefore, a post-translational modification is contemplated for causing lower expression of HEART1.

Alternatively, therapeutic interventions using HEATR1 is contemplated to improve outcome in combination with existing therapies. Because Gemcitabine represents the standard of care for PDAC, a combination therapy using an Akt inhibitor and Gemcitabine using HEATR1 as a biomarker for guiding the use of this therapy is contemplated for use in the present inventions. However, it is not meant to limit the Akt inhibitor or chemotherapeutic. In fact, any of the Akt inhibitors mentioned herein, in addition to known Akt inhibitors for pAkt308 are contemplated for use with HEARTR1 for treating pancreatic cancer. Any of the chemotherapeutics mentioned herein or known are contemplated for use with HEARTR1 for treating pancreatic cancer. Biochemically, HEATR1 Affects Pancreatic Cancer Cell Response to Chemotherapy by Negatively Regulating Akt.

HEATR1 expression levels were shown to affect survival of pancreatic cancer cells to chemotherapy associated with specific changes in Akt activity. Moreover, HEATR1 was then shown to function as a scaffold protein to regulate Akt phosphorylation by PP2A. Thus, HEATR1 is an Akt regulator and is contemplated to provide prognosis information and a response predictor for PDAC patients.

The inventors describe that treating pancreatic cancer cells with an Akt inhibitor triciribine (TCN) which sensitized HEATR1 depleted cells to Gemcitabine treatment, both in vitro and in animal models (FIG. 4A and FIG. 3B-D), respectively, showing that a combination therapy of an Akt inhibitor and Gemcitabine, overcame Gemcitabine resistance. Thus, a similar treatment is contemplated in patients with low HEATR1 expression. The HEATR1 gene also associates with response to a chemotherapeutic drug 1-beta-d-arabinofuranosylcytosine (Ara C), oxaliplatin, mitomycin C, SN-38, etoposide Camptothecin and paclitaxel.

Further experimental data showed that when HEATR1 was artificially downregulated with siRNA in SU86, PANC-1 and ASPC-1 cells, an increase in resistance to Gemcitabine was shown in these three lines. Similar results were obtained when two shRNA with a different targeting sequence to downregulate HEATR1 were used.

Additionally, multiple classes of chemotherapeutic drugs including oxaliplatin, SN-38 (active metabolite of topoisomerase I inhibitors), mitomycin c (MMC), paclitaxel (microtubule stabilizer), Camptothecin and etopside were used to treat HEATR1 knockdown SU86 cells. Similar to Gemcitabine, cells having reduced HEATR1 expression were significantly resistant to these chemotherapeutic drugs. In contrast, Gemcitabine induced higher levels of apoptosis in control cells than in cells transfected with HEART1 shRNA.

HEATR1 Regulates Akt Phosphorylation at Thr308 by Promoting Akt-PP2AB56β Interaction.

During the development of the present inventions, the downregulation of HEATR1 using its specific siRNA or shRNA led to the discovery of an increased phosphorylation of Akt at Thr308, but no effect on the phosphorylation of Ser473. Results of experiments, see below, indicated that HEATR1 is a protein that promotes the de-phosphorylation of Akt at Thr308. Wild-type (WT) HEATR1 decreased Akt phosphorylation at Thr308 and decreased cellular sensitivity to Gemcitabine, while HEATR1 mutants that abolish Akt interaction failed to do so. Therefore the inventors' determined whether the AKT308 effect was further related to apoptotic pathways.

Because Gemcitabine induced stronger apoptosis activity in control cells than in cells transfected with HEATR1 shRNA (FIG. 8A), the inventors' sought a link between pathways regulating cell death and HEATR1 affects on chemotherapy responses. Gemcitabine induced strong expression of c-PARP1 in control cells than in cells transfected with HEATR1 shRNA as shown by a reduction of c-PARP1 (FIG. 8A). In particular, two HEATR1 specific shRNAs demonstrated that by reducing HEATR1 in Gemcitabine treated cells then c-PARP1 was also reduced as is the amount of apoptosis thus allowing increased cell numbers (FIG. 8B).

Further, we found that downregulation of HEATR1 led to an increased phosphorylation of Akt at Thr308, but not at Ser473 (FIG. 2A-B). These results suggest that depletion of HEATR1 affects steady state Akt phosphorylation, which is consistent with an increase in cell growth (FIG. 7B). We next examined how HEATR1 affects acute Akt activation. Cells were starved and stimulated with serum. Phosphorylation of Akt Thr308 and the Akt substrate GSK-3β were significantly increased in cells transfected with HEATR1 siRNA (FIG. 2C). Furthermore, overexpression of HEATR1 decreased phosphorylation of Akt at Thr308, but not Ser473 (FIG. 2D). We also found that HEATR1 interacted with Akt in cells (FIG. 2E-F). The intracellular co-localization of HEATR1 and Akt were detected by confocal microscopy. Akt and HEATR1 colocalize in the cytoplasm and occasionally at the cell membrane in most cells examined (FIG. 9A).

Since HEATR1 specifically regulates phosphorylated at Thr308, signaling events that directly control Akt phosphorylation at Thr308 were identified during the development of the present inventions. Thr308 of Akt can be phosphorylated by PDK1 and dephosphorylated by PP2A (16, 18, 27). However, no apparent difference of PDK1 (FIG. 2C). HEATR1 neither interacted with PDK1 nor affected the interaction between Akt and PDK1 (FIG. 9B-C), indicating HEATR1 regulates Akt activity independent of PDK1. Next, we examined whether HEATR1 regulates Thr308 phosphorylation through PP2A. Treatment of PP2A inhibitor okadaic acid significantly increased Akt phosphorylation at Thr308, and HEATR1 knockdown did not further increase Thr308 phosphorylation (FIG. 9D).

As shown in FIG. 2G, HEATR1 interacted with PP2A scaffolding subunit Aα, catalytic subunit Cα and regulatory subunits B55α and B56β, which have been reported to specifically target Akt Thr308 dephosphorylation (16-18, 27). Furthermore, purified HEATR1 only interacted with recombinant GST-B56β, suggesting a direct interaction between HEATR1 and B56β (FIG. 2H). Because HEATR1 interacts with both Akt and B56β and regulates Akt phosphorylation, we hypothesized that HEATR1 may function as a scaffolding protein to facilitate Akt dephosphorylation by PP2A. Downregulation of HEATR1 decreased the interaction between B56β and Akt (FIG. 2I), while HEATR1 overexpression increased it (FIG. 2J). Furthermore, purified FLAG-HEATR1 increased the interaction between recombinant His-Akt1 and GST-B56β (FIG. 2K). These results suggest that HEATR1 promotes the interaction between Akt and PP2A, facilitating the dephosphorylation of Akt at Thr308.

HEATR1 Regulates Akt Phosphorylation and Cell Response to Gemcitabine Through its Scaffolding Function.

To investigate specific regions of HEATR1 for Akt and B56β interaction, we generated deletion mutants of HEATR1 (FIG. 3A). N-terminal region (aa 1-420) was essential for the binding of HEATR1 with B56β; while the middle region (420-1420) was responsible for the binding of HEATR1 with Akt (FIG. 3B-C). These results suggest that HEATR1 binds Akt and B56β using different regions. To further confirm that the scaffolding function of HEATR1 is related to the regulation of Akt phosphorylation, we overexpressed WT and mutants in cells (FIG. 3D). WT decreased Akt phosphorylation at Thr308 and cellular sensitivity to Gemcitabine, while HEATR1 mutants that abolish Akt or B56β interaction failed to do so (FIG. 3D-E). These results suggest that HEATR1 regulates Akt phosphorylation and cell response to Gemcitabine through its scaffolding function.

Surprisingly Akt308 Phosphorylation (pAkt308) is a Biomarker Along with HEATR1 for Patients with Pancreatic Ductal Adenocarcinoma (PDAC).

Tissues from pancreatic ductal adenocarcinoma and peritumoral pancreatic tissues obtained from 100 PDAC patients who had undergone radical resection revealed that expression of HEATR1 was significantly lower in pancreatic tumor tissue than in normal pancreatic tissues. On the other hand, the staining of Akt phosphorylation at Thr308 was significantly higher in pancreatic tumor tissue than in normal pancreatic tissue. PDAC patients with high HEATR1 expression or low AKT308 phosphorylation in tumors had a significant improvement in overall survival after receiving standardized Gemcitabine chemotherapy. Based on the IOD value there is a negative significant correlation of expression of HEATR1 and Akt phosphorylation at Thr308 in tumor tissues. Surprisingly, a significant correlation was shown between the Akt308 expression and TNM staging and lymph node metastasis, whereas there was no correlation between HEATR1 expression and clinical pathological features. Therefore, the inventors contemplate the use of HEATR1 expression and Akt308 phosphorylation together as biomarkers and as potentially independent prognostic factors.

Association of HEATR1 Expression, with Our without Corresponding pAKT308 Levels in Pancreatic Cancer Patients, with Survival and Response to Chemotherapy.

Figure 6:
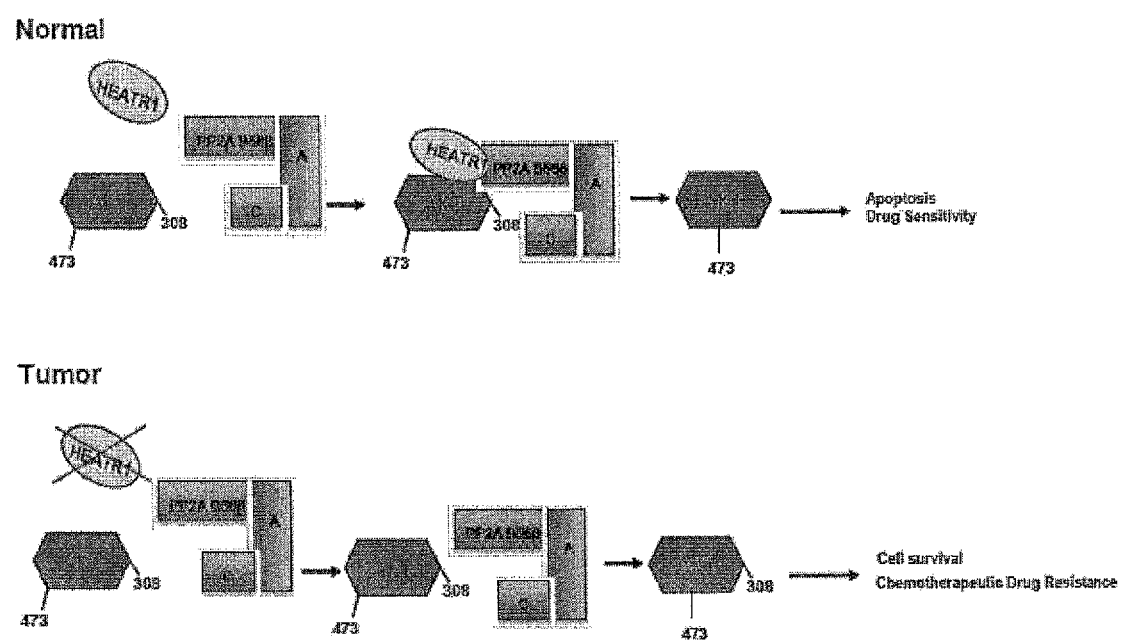
FIG. 6 shows an exemplary 'Experimental Model'.

Clinical samples were used to examine the role of HEATR1 in clinical responses. Among 100 patients with PDAC, 76 patients died and 24 patients survived, with the median survival time of 18 months. Pathological analysis using pancreatic ductal adenocarcinoma and peritumoral tissues from patients were performed. Statistical analysis revealed that expression of HEATR1 was significantly lower in pancreatic tumor tissue than in normal pancreatic tissues (FIG. 5A). The staining of Akt phosphorylation at Thr308 was significantly higher in pancreatic tumor tissue than in normal pancreatic tissue (FIG. 5A). Furthermore, low HEATR1 proteins levels correlates with increased Akt phosphorylation at Thr308 in representative pancreatic cancer samples (FIG. 5B). We next evaluated whether HEATR1 expression was associated with the response of patients to standardized Gemcitabine chemotherapy. As shown in FIG. 5C-D; FIG. 10 and Table 3, PDAC patients with high HEATR1 or low AktT308 expression in tumors had a significant improvement in overall survival. Thus, determination of HEATR1 expression in PDAC tissues may be useful as an independent predictor for Gemcitabine response. Based on IOD value, we observed a negative correlation between HEATR1 expression and Akt phosphorylation at Thr308 in tumor tissues (FIG. 5E). Meanwhile, we observed a significant correlation between the Akt308 phosphorylation and TNM staging, lymph node metastasis, whereas we did not find the correlation between HEATR1 expression and clinical pathological feature (Table 1). From multivariate survival analysis, HEATR1 expression and Akt308 phosphorylation might be independent prognostic factors among these variables (Table 2). Overall, these results showed that HEATR1 negatively regulates Akt activation and upregulation of Akt activity by loss of HEATR1 in pancreatic cancers might give rise to the resistance to chemotherapy (FIG. 6).

Akt: A Serine/Threonine Protein Kinase.

Akt (also Protein kinase B (PKB or PKB/Akt)) is a protein known to regulate cell proliferation and survival, angiogenesis and glucose metabolism (1, 2). The Akt pathway, is a hyperactivated signaling pathway found in many human cancers, involved with both tumorigenesis and chemo-resistance. In fact, aberrant Akt activation is associated with diverse pathophysiological states including cancers and chemoresistance (3, 4). Activation of Akt occurs when Akt has phospho-Thr308 and/or phospho-Ser473. Both pThr308 and pSer473 are required for the full activation of Akt activity.

Using pAkt308 as a Biomarker for Pancreatic Adenocarcinoma (PDAC).

Previously, half of tested pancreatic adenocarcinomas tumors demonstrated activation of Akt by immunohistochemical staining of pAkt (31). Further, significant correlation between activation of Akt and poor patient survival suggested a role of Akt activation in pancreatic cancer (32). Moreover, Akt and the amount of Akt308 phosphorylation were measured in experiments using Akt inhibitors as treatment for pancreatic cancer, i.e. for testing their effects on pancreatic cancer cells lines and tumors arising from these cell lines. However, none of these references described measuring higher levels of pAkt308 alone, or in combination with measuring HEATR1, in pancreatic ductal adenocarcinoma cancer specifically for guidance in administering or changing a specific treatment.

The following references are a few examples of the presence or use of pAkt as biomarkers for pancreatic cancer. In, Mortenson, et al., "AKT: A novel target in pancreatic cancer therapy. Review Article." Cancer Therapy Vol 2, 227-238 (2004), 59% of combined localized/resected tumors and metastatic tumors showed activation of pAkt by immunohistochemical staining. Akt activation correlated with histological grade indicating the involvement of pAkt in more aggressive tumors. Survival analysis of patients was performed and demonstrated a significant correlation between activation of Akt and poorer survival. The 5-year survival rate was only 16.4 months for patients whose tumors demonstrated activation of Akt, but 50.6 months for patients whose tumors did not demonstrate activated Akt. Further, Akt was described as subsequently activated by phosphorylation on Thr308 in relation to HER-2/neu oncogene expression. A combined therapy of HER-2/neu oncogene inhibition which reduces pAkt in combination with Gemcitabine was suggested for use in the subset of pancreatic cancer patients whose tumors overexpress HER-2/neu.; WO 2006119980 A1. "Determination of responders to chemotherapy." Published Nov. 16, 2006, describes a method of using levels of phosphorylated Akt protein (pAkt) as a biomarker for selecting a composition, including a chemotherapeutic agent, for inhibiting the progression of lung cancer or alternatively, pancreatic cancer and unspecified adenocarcinoma, in a patient. In particular, determining overexpression of a phosphorylated Akt protein in the biological sample indicates whether cancer cells are sensitive to a combination of an epidermal growth factor receptor inhibitor and a chemotherapeutic agent. Specifically, for pancreatic cancer a chemotherapeutic agent is Gemcitabine and/or cisplatin. The reference describes three isoforms of Akt 1-3 phosphorylated (pAKT) in a similar fashion at residues T308 in the activation domain and S473 in the COOH-terminal domain but then describes phosphorylation of Akt1/PKBα occurring on two sites $Thr^{308}$ and on $Ser^{473}$, Akt2/PKBbeta ($Thr^{309}$ and $Ser^{474}$) and Akt3/PKBgamma ($Thr^{305}$ and $Ser^{472}$). For patients treated with chemotherapy/placebo "positive" pAKT expression is associated with a worse prognosis. Thus, positive pMAPK" patients might benefit from the chemotherapy/Tarceva® combo. "Negative" pAkt expression appears to be associated with longer survival; Meuillet, et al. "Molecular pharmacology and antitumor activity of PHT-427, a novel Akt/phosphatidylinositide-dependent protein kinase 1 pleckstrin homology domain inhibitor." Mol Cancer Ther. 9:706-717 (2010), describes a decrease in activated Akt and pAkt308 were associated with antitumor activity of a small molecule i.e. PHT-427 inhibitor of Akt/PDK1, when used for treating human pancreatic cancer cells and xenografts in mice. A decrease of phospho-Thr308-Akt and phospho-Ser473 was observed for Akt inhibitor sensitive but not Akt inhibitor resistant human pancreatic cancer cells. Moreover, PHT-427 treatment of resistant cancer cells showed an increase in Akt activity. In contrast to in vivo studies where PHT-427 decreased Akt phospho-Thr308 and phospho-Ser473 in both types of tumors yet only the Akt sensitive cell tumors showed a reduction in growth rates. Thus, an additional factor controlled the tumor response to the PHT-427 inhibitor.

Akt Control of Cell Functions.

Akt controls cellular functions through phosphorylating substrates. Akt directly phosphorylates BAD, preventing it from inhibiting prosurvival Bcl-2 family members (5, 6). Akt regulates glucose metabolism through phosphorylating and inactivating GSK3 (7). In addition, Akt negatively regulates FOXO and p53 and blocks the transcription of BIM, Puma and Noxa (8, 9). Furthermore, Akt promotes protein synthesis and cell growth through activation of mammalian target of rapamycin (10).

Akt activity is tightly controlled at multiple levels. Phosphoinositide 3-kinase (PI-3K), a critical upstream kinase of Akt signaling, is activated by growth factors, cytokine and other factors or stimuli (2) and converts phosphatidylinositol-4,5-bisphosphate (PIP2) to phosphatidylinositol-3,4,5-trisphosphate (PIP3). PIP3 recruits Akt to plasma membrane, where Akt is phosphorylated at Thr308 (11). Ubiquitination of Akt by TRAF6 and Skp2-SCF E3 ligase is required for the recruitment of Akt to plasma membrane (12, 13). Full Akt activity requires phosphorylation of both Thr308 and Ser473 mediated by phosphoinositide-dependent kinase 1 (PDK1) (14) and mammalian target of rapamycin (mTOR) complex 2 (mTORC2) (15), respectively. On the other hand, protein phosphatase 2A (PP2A) (16-18) and PH domain leucine-rich repeat protein phosphatase (PHLPP) (19, 20) dephosphorylate AktThr308 and Ser473, respectively. FKBP51 promotes dephosphorylation of Akt Ser473 through acting as a scaffolding protein for Akt and PHLPP (21). However it is not known how Akt physically interacts with PP2A.

Akt Inhibitor Sensitizes Pancreatic Cells with HEATR1 Knockdown to Gemcitabine.

The results described above suggest that HEATR1 regulates Gemcitabine sensitivity at least partly through regulating Akt and hyperactivation of Akt in cells with low HEATR1 level might be responsible for increased chemoresistance. If this was the case, treating cells with an Akt inhibitor should reverse chemoresistance in cells depleted of HEATR1. TCN-P, the active metabolite of Akt inhibitor triciribine (TCN), binds to PH domain of Akt and prevents its recruitment to cell membrane, where Akt is phosphorylated by PDK1 at Thr308 (28). When TCN was used alone, no significant difference of cytotoxicity and apoptosis was observed in different cell lines transfected with control and HEATR1 siRNA (FIG. 10A-E). In addition, TCN did not significantly affect Gemcitabine sensitivity and apoptosis in control cells. However, TCN sensitized cells depleted of HEATR1 to Gemcitabine (FIG. 4A-B; FIG. 10B-E). We next tested whether addition of TCN would reverse chemoresistance of tumors with low HEATR1 level in vivo. Xenograft experiments showed that downregulation of HEATR1 promoted tumor growth and resistance to Gemcitabine (FIG. 4C-E and FIG. 10F). TCN treatment resensitized these cells' response to Gemcitabine. This is consistent with in vitro results using pancreatic cancer cell lines and indicates that HEATR1 affects chemosensitivity through regulating Akt activity in vivo.

Treatment of Pancreatic Adenocarcinoma (PDAC) Patients with an AKT Inhibitor and a Chemotherapeutic Agent for Treating a Pancreatic Cancer Patient.

Targeted inhibition of Akt alone or combined with a chemotherapeutic agent is described in numerous references and may find use with biomarkers HEATR1 and/or pAkt308 as described in the present inventions. Currently, several small molecule inhibitors of Akt were developed and are in various stages of clinical testing (33). For examples, a cyclin-dependent kinase inhibitor (dinaciclib) combined with the oral pan-Akt Inhibitor MK-2206 can dramatically block pancreatic tumor growth and metastases in patient-derived xenograft models (34). Phase I trial results of MK-2206 in patients with advanced solid tumors indicate that MK-2206 was well tolerated, with evidence of Akt signaling blockade (35). RX-0201, an antisense oligonucleotide to mRNA encoding Akt1, in combination with Gemcitabine were investigated in a phase II study and the safety and efficacy results are awaited (36). Further, exemplary references described below combine an Akt inhibitor with a chemotherapeutic. In, Reddy Boreddy, et al., "Pancreatic Tumor Suppression by Benzyl Isothiocyanate Is Associated with Inhibition of PI3K/AKT/FOXO Pathway." Clin Cancer Res 17; 1784 (2011), describes that many chemo-drugs are known to acquire resistance by activating Akt proteins, such as gemcitabine treatment that results in pancreatic cancer that acquires drug resistance due to hyperactivation of the PI3K/Akt survival pathway. Benzyl isothiocyanate (BITC; suppresses the phosphorylation of Akt at both Ser-473 and Ser-308) was administered together with LY-294002 (an inhibitor of the PI3K/AKT/FOXO pathway) which suppressed the growth of human pancreatic cell lines and a human pancreatic tumor, in vitro and in vivo (xenograft mice), respectively. Thus, Benzyl isothiocyanate, an inhibitor of Akt, is suggested for use in treatment along with traditional chemotherapy, where the therapeutic itself causes activation of Akt proteins; WO 2009032651. "Inhibitors of AKT activity." Published Mar. 12, 2009, describes treating pancreatic cancers, including Akt2 overexpressing pancreatic cancers, using inhibitors of protein kinase B (alternatively PKB/Akt, PKB or Akt). Pharmaceutically active inhibitor compounds were suggested to be co-administered with further active ingredients, such as other compounds known to treat cancer or compounds known to have utility when used in combination with an Akt inhibitor; U.S. Pat. No. 8,828,451. "AKT Sensitization of Cancer Cells." Published Sep. 9, 2014, describes cells lines treated with combinations of Akt activation inhibitor Triciribine (TCN) or Triciribine phosphate (TCNP) and chemotherapeutic drugs to overcame cytotoxic or treatment resistance; Fahy, et al., "AKT inhibition is associated with chemosensitisation in the pancreatic cancer cell line MIA-PaCa-2." British Journal of Cancer 89:391-397 (2003), is a review of using Akt inhibitors with chemotherapeutic agents. Inhibition of activation of the serine/threonine kinase Akt, a target of PI3K, was described as sensitizing cells to the apoptotic effect of chemotherapy and suggested co-administration for improving the efficacy of standard chemotherapeutic agents.

In contrast, Chen, et al., "Inhibition of AKT2 Enhances Sensitivity to Gemcitabine via Regulating PUMA and NF-κB Signaling Pathway in Human Pancreatic Ductal Adenocarcinoma." Int. J. Mol. Sci. 13(1), 1186-1208 (2012), describes that the level of Akt activation is not likely to be useful in selecting individual pancreatic tumors for Akt inhibition in combination with gemcitabine. Akt2 inhibition using an siRNA inhibitor sensitized some, but not all, of the pancreatic cancer cell lines to Gemcitabine-induced apoptosis. Thus, Akt inhibitors may have therapeutic potential when used in combination with gemcitabine in reversing drug resistance in some pancreatic cancer patients. In fact, the discovery described herein of HEATR1 as a biomarker for resistance to Gemcitabine may explain why the use of Akt inhibitors in combination with Gemcitabine does not reverse drug resistance in these pateints.

Summary

HEATR1 was show herein as a negative regulator of the Akt pathway in PADC. Diagnostic studies showed that lower expression levels of HEATR1 is a biomarker for predicting chemoresistance of cells and patient outcome. Additionally, HEATR1 expression levels affects cellular response to other chemotherapeutic agents. Furthermore, HEATR1 expression in combination with levels of pAk308, i.e. lower HEATR1 and higher pAkt308, normal HEATR1 and low pAkt308, is contemplated for use in guiding a change in therapy for PDAC patients. Further, levels of pAkt308 are contemplated for guiding changes in therapy for PDAC patients.

Table 1. Relationship Between Expression of Tumoral HEATR1 & pAkt T308 and Clinicopathological Features.
Table 2. Univariate and Multivariate Analyses of Factors Associated with Survival.
Table 3. Total Survival of Pancreatic Cancer Patients.

TABLE 1

Relationship between expression of tumoral HEATR1 & pAkt T308 and clinicopathological features.

| Clinicopathological Features | Tumoral expression of HEATR1 | | | Tumoral expression of pAkt T308 | | |
|---|---|---|---|---|---|---|
| | Low. | High. | P | Low. | High. | P |
| Age, years | | | 0.229 | | | 0.422 |
| <60 | 20 | 26 | | 25 | 21 | |
| >=60 | 30 | 24 | | 25 | 29 | |
| Gender | | | 0.84 | | | 0.069 |
| Male | 29 | 28 | | 33 | 24 | |
| Female | 21 | 22 | | 17 | 26 | |
| Tumor location | | | 0.476 | | | 0.812 |
| Head | 10 | 13 | | 12 | 11 | |
| distal | 40 | 37 | | 38 | 39 | |
| Differentiation level | | | 0.579 | | | 0.423 |
| low | 24 | 26 | | 26 | 22 | |
| high | 24 | 26 | | 24 | 28 | |
| Lymph node metastasis | | | 0.688 | | | 0.005 |
| no | 26 | 28 | | 34 | 20 | |
| yes | 24 | 22 | | 16 | 30 | |
| Neural invasion | | | 0.592 | | | 0.061 |
| no | 12 | 12 | | 16 | 8 | |
| yes | 38 | 38 | | 34 | 42 | |
| Vascular metastasis | | | 0.505 | | | 0.505 |
| no | 46 | 44 | | 46 | 44 | |
| yes | 4 | 6 | | 4 | 6 | |
| TNM staging | | | 0.583 | | | 0.01 |
| I | 8 | 12 | | 12 | 8 | |
| IIA | 19 | 16 | | 23 | 12 | |
| IIB | 23 | 22 | | 15 | 30 | |

TABLE 2

Univariate and multivariate analyses of factors associated with survival.

| | | OS | | |
|---|---|---|---|---|
| | | | Multivariate | |
| Factor | Univariate P | Hazard Ratio | 95% CI | P |
| Age, y (>=60 vs <60) | 0.301 | — | — | NA |
| Gender (female vs male) | 0.353 | — | — | NA |
| Tumor location (head vs distal) | 0.147 | — | — | NA |
| Differentiation level (high vs low) | 0.162 | — | — | NA |
| Lymph node metastasis (yes vs no) | 0.001 | — | — | NS |
| Neural invasion (yes vs no) | 0.011 | — | — | NS |
| Vascular metastasis (yes vs no) | 0.369 | — | — | NA |
| TNM staging (I, IIA,IIB) | 0.006 | — | — | NS |
| HEATR1 expression in tumor | 0.002 | 0.549 | 0.339-0.887 | 0.014 |
| pAkt T308 expression in tumor | 0.000 | 6.379 | 3.605-11.288 | 0.000 |

(OS, overall survival; NA, not adopted; NS, not significant)

TABLE 3

Total survival of pancreatic cancer patients.

| HEATR1 | Patient number | Patients of Events | | Censored Percent |
|---|---|---|---|---|
| | | Death | Alive | |
| Strong | 28 | 14 | 14 | 50.0% |
| Weak | 72 | 62 | 10 | 13.8% |
| Overall | 100 | 76 | 24 | 24.0% |

REFERENCES

1. Bellacosa, et al., Activation of AKT kinases in cancer: implications for therapeutic targeting. Advances in cancer research. 2005; 94:29-86.
2. Manning B D, Cantley L C. AKT/PKB signaling: navigating downstream. Cell. 2007; 129:1261-74.
3. Altomare D A, Testa J R. Perturbations of the AKT signaling pathway in human cancer. Oncogene. 2005; 24:7455-64.
4. Jazirehi, et al., Therapeutic implications of targeting the PI3Kinase/AKT/mTOR signaling module in melanoma therapy. American journal of cancer research. 2012; 2:178-91.
5. Datta, et al., Akt phosphorylation of BAD couples survival signals to the cell-intrinsic death machinery. Cell. 1997; 91:231-41.
6. del Peso, et al., Interleukin-3-induced phosphorylation of BAD through the protein kinase Akt. Science. 1997; 278:687-9.
7. Cross, et al., Inhibition of glycogen synthase kinase-3 by insulin mediated by protein kinase B. Nature. 1995; 378:785-9.
8. Brunet, et al., Akt promotes cell survival by phosphorylating and inhibiting a Forkhead transcription factor. Cell. 1999; 96:857-68.
9. Happo, et al., Maximal killing of lymphoma cells by DNA damage-inducing therapy requires not only the p53 targets Puma and Noxa, but also Bim. Blood. 2010; 116:5256-67.
10. Vander Haar, et al., Insulin signalling to mTOR mediated by the Akt/PKB substrate PRAS40. Nat Cell Biol. 2007; 9:316-23.
11. Brazil D P, Hemmings B A. Ten years of protein kinase B signalling: a hard Akt to follow. Trends in biochemical sciences. 2001; 26:657-64.
12. Chan, et al., The Skp2-SCF E3 ligase regulates Akt ubiquitination, glycolysis, herceptin sensitivity, and tumorigenesis. Cell. 2012; 149:1098-111.
13. Yang, et al., The E3 ligase TRAF6 regulates Akt ubiquitination and activation. Science. 2009; 325:1134-8.
14. Alessi, et al., Characterization of a 3-phosphoinositide-dependent protein kinase which phosphorylates and activates protein kinase Balpha. Current biology: CB. 1997; 7:261-9.
15. Sarbassov, et al., Phosphorylation and regulation of Akt/PKB by the rictor-mTOR complex. Science. 2005; 307:1098-101.
16. Padmanabhan, et al., A PP2A regulatory subunit regulates *C. elegans* insulin/IGF-1 signaling by modulating AKT-1 phosphorylation. Cell. 2009; 136:939-51.
17. Rodgers, et al., Clk2 and B56beta mediate insulin-regulated assembly of the PP2A phosphatase holoenzyme complex on Akt. Molecular cell. 2011; 41:471-9.
18. Kuo, et al., Regulation of phosphorylation of Thr-308 of Akt, cell proliferation, and survival by the BS55alpha regulatory subunit targeting of the protein phosphatase 2A holoenzyme to Akt. The Journal of biological chemistry. 2008; 283:1882-92.
19. Gao, et al., PHLPP: a phosphatase that directly dephosphorylates Akt, promotes apoptosis, and suppresses tumor growth. Molecular cell. 2005; 18:13-24.
20. Brognard, et al., PHLPP and a second isoform, PHLPP2, differentially attenuate the amplitude of Akt signaling by regulating distinct Akt isoforms. Molecular cell. 2007; 25:917-31.
21. Pei, et al., FKBP51 affects cancer cell response to chemotherapy by negatively regulating Akt. Cancer cell. 2009; 16:259-66.
22. Groves, et al., The structure of the protein phosphatase 2A PR65/A subunit reveals the conformation of its 15 tandemly repeated HEAT motifs. Cell. 1999; 96:99-110.
23. Wu, et al., Glioma-associated antigen HEATR1 induces functional cytotoxic T lymphocytes in patients with glioma. Journal of immunology research. 2014; 2014: 131494.
24. Azuma, et al., Perturbation of rRNA synthesis in the bap28 mutation leads to apoptosis mediated by p53 in the zebrafish central nervous system. J Biol Chem. 2006; 281:13309-16.
25. Dima, et al., An exploratory study of inflammatory cytokines as prognostic biomarkers in patients with ductal pancreatic adenocarcinoma. Pancreas. 2012; 41:1001-7.
26. Li, et al., Gemcitabine and cytosine arabinoside cytotoxicity: association with lymphoblastoid cell expression. Cancer Res. 2008; 68:7050-8.
27. Ruvolo, et al., Low expression of PP2A regulatory subunit B55alpha is associated with T308 phosphorylation of AKT and shorter complete remission duration in acute myeloid leukemia patients. Leukemia. 2011; 25:1711-7.
28. Berndt, et al., The Akt activation inhibitor TCN-P inhibits Akt phosphorylation by binding to the PH domain of Akt and blocking its recruitment to the plasma membrane. Cell Death Differ. 2010; 17:1795-804.
29. Costello, et al., New biomarkers and targets in pancreatic cancer and their application to treatment. Nat Rev Gastroenterol Hepatol. 2012; 9:435-44.
30. Stathis A, Moore M J. Advanced pancreatic carcinoma: current treatment and future challenges. Nature reviews Clinical oncology. 2010; 7:163-72.
31. Schlieman, et al., Incidence, mechanism and prognostic value of activated AKT in pancreas cancer. Br J Cancer. 2003; 89:2110-5.
32. Yamamoto, et al., Prognostic significance of activated Akt expression in pancreatic ductal adenocarcinoma. Clin Cancer Res. 2004; 10:2846-50.
33. Pal, et al., Akt inhibitors in clinical development for the treatment of cancer. Expert Opin Investig Drugs. 2010; 19:1355-66.
34. Hu, et al., Combined Inhibition of Cyclin-Dependent Kinases (Dinaciclib) and AKT (MK-2206) Blocks Pancreatic Tumor Growth and Metastases in Patient-Derived Xenograft Models. Mol Cancer Ther. 2015; 14:1532-9.
35. Yap, et al., First-in-man clinical trial of the oral pan-AKT inhibitor MK-2206 in patients with advanced solid tumors. J Clin Oncol. 2011; 29:4688-95.
36. A Safety and Efficacy Study of RX-0201 Plus Gemcitabine in Metastatic Pancreatic Cancer. NCT01028495.
37. Misek, et al., Early detection and biomarkers in pancreatic cancer. Journal of the National Comprehensive Cancer Network: JNCCN. 2007; 5:1034-41.

EXPERIMENTAL

The following examples serve to illustrate certain embodiments and aspects of the present invention and are not to be construed as limiting the scope thereof.

In the experimental disclosures which follow, the following abbreviations apply: N (normal); M (molar); mM (millimolar); microM (micromolar); mol (moles); mmol (millimoles); micro.mol (micromoles); nmol (nanomoles); pmol (picomoles); g (grams); mg (milligrams); microg (micro-grams); ng (nanograms); pg (picograms); L and (liters); ml (milliliters); microl (microliters); cm (centimeters); mm (millimeters); microm (micrometers); nm (nanometers); U (units); min (minute); s and sec (second); deg (degree); and ° C. (degrees Centigrade/Celsius).

Example I

The following are exemplary materials and methods used herein.

Cell Culture and Plasmids.

Human pancreatic cancer cell lines SU86.86, ASPC-1, and PANC-1 were purchased from ATCC in 2014. The identities of these cell lines were confirmed by the medical genome facility at Mayo Clinic Center using short tandem repeat profiling upon receipt. The cell lines were maintained in RPMI 1640 with 10% FBS. HEATR1 cDNA was purchased from Thermo Scientific and full length and mutants were subcloned into pIRES-EGFP. PP2A-Aα, B55α, B56β, Cα were purchased from addgene and subcloned into HA-pcmv and pGex4T-1. HEATR1 siRNA and shRNA were from Dharmacon and Sigma, respectively.

Methanethiosulfonate (MTS) Assay.

Gemcitabine was from Eli Lilly (Indianapolis, Ind.). Paclitaxel, SN-38, mitomycin c, oxaliplatin and etopside were from Sigma-Aldrich (St. Louis, Mo.). Triciribine was from EMD Biosciences (San Diego, Calif.). Ctrl (Control) or HEATR1 siRNA or shRNA were transfected, and the growth-inhibitory effect was performed as described previously (21). In one embodiment, a MTS assay may be performed by a MTS Cell Proliferation Assay Kit (Colorimetric) (197010); a colorimetric sensitive quantification of viable cells in proliferation and cytotoxicity assays. The assay is based on the reduction of MTS tetrazolium compound by viable cells to generate a colored formazan product that is soluble in cell culture media.

Tumor Xenograft Study.

Female athymic nu/nu mice were obtained from the National Cancer Institute. Experiments were performed under the approval of the Institutional Animal Care and Use Committee at Mayo Clinic. PANC-1 cells stably expressing Ctrl and HEATR1 shRNA were injected subcutaneously in mouse flanks ($10^6$ cells/mouse flank). Tumor volumes were measured every three days. When tumors reached 100 mm$^3$, mice were randomized to four groups (n=8): vehicle; TCN (0.5 mg/kg/day), administered i.p. once daily; Gemcitabine (50 mg/kg), administered i.p. every 3 days; a combination of two treatments. After sacrificing the mice, tumors were surgically removed and weighted.

Patients' Specimens and Follow-Up.

From 2007 to 2012, the same surgical team in our institute, i.e. the National Cancer Institute, performed curative resection for pancreatic cancer on 100 consecutive patients, defined as macroscopically complete removal of the tumor. Patients were observed until February 2014. Overall survival (OS) was defined as the interval between the date of surgery and death. None of the patients received any type of preoperative anticancer treatment. The patients received standardized postoperative chemotherapeutic regimen of Gemcitabine. Of the clinicopathological features, tumor stage was determined according to the 2002 International Union Against Cancer TNM classification system. Tumor differentiation was graded by the Edmondson grading system. The study was approved by the Zhongshan Hospital Research Ethics Committee.

Immunohistochemical Staining and Image Analysis.

A tissue microarray was constructed following standard tissue array producing protocols as described previously (25). Primary antibodies were both rabbit polyclonal antibody for HEATR1 and pAkt308, followed by incubation with the secondary antibody. High-sensitivity diaminobenzidine chromogenic substrate system was used for colorimetric visualization. The density of positive staining was measured by a computerized image system including Leica-CCD camera connected to a Leica-DM-IRE2 microscope. Under high-power magnification, photographs of representative fields were captured by the Leica QWin Plus v3 software. HEATR1 density was counted by Image-Pro Plus v6.2 software.

Statistical Analysis.

Data were presented as mean±SD and analyzed using t-test or ANOVA. Significance was set at $p<0.05$. SPSS 16.0 for Windows (SPSS Inc) were used for survival analysis in patients; Pearson $\chi^2$ test or Fisher's exact test was used to compare qualitative variables; and quantitative variables were analyzed by t test or Pearson's correlation test. Kaplan-Meier analysis was used to determine the survival. Log-rank test was used to compare patients' survival between subgroups; the Cox regression model was used to perform multivariate analysis.

Supplemental Methods

Antibodies.

Antibodies against Akt (9272), phospho-Akt(Thr308) (9275), phospho-Akt(Ser473) (9271), GSK3β (9315), phospho-GSK3β (9336), PDK1 (3062), phospho-PDK1 (3061), PP2A Aα (2039), B55α (4953), Cα (2038) and cleaved PARP1 (5625) were purchased from Cell Signaling. Anti-HEATR1 antibody was generated with GST fusion protein of HEATR1 (1894-2144). Anti-FLAG (F3165), anti-HA (H3663) and anti-β-actin (A2228) antibodies were purchased from Sigma. Mouse anti-Akt (2920) used for immunofluorescence staining were purchased from Cell Signaling. Anti-HEATR1 (HPA046917) and anti-phospho Akt (Thr308) (SAB4504332) antibodies used for immunohistochemical staining were obtained from Sigma.

Immunoprecipitation, Immunoblotting, and In Vitro Pull-Down Assay.

We prepared cell lysates, performed immunoprecipitation, and immunoblotting as previously described. In brief, cells were lysed with NETN buffer (20 mM Tris-HCl, pH 8.0, 100 mM NaCl, 1 mM EDTA, 0.5% Nonidet P-40) containing 50 mM b-glycerophosphate, 10 mM NaF, and 1 mg/ml each of pepstatin A and aprotinin. Whole cell lysates were pulse-sonicated and obtained by centrifugation. Whole cell lysates were incubated with 2 μg of antibody and protein A or protein G Sepharose beads (Amersham Biosciences) for 2 hr or overnight at 4° C. The immunocomplexes were then washed with NETN buffer for three times and separated by SDS-PAGE. Immunoblotting was performed following standard procedures. GST fusion proteins were bound to glutathione-Sepharose overnight at 4° C. The beads were washed with PBS four times and incubated with cell lysates for 1 h at 4° C. After washing with NETN for three times, the bound proteins were separated by SDS-PAGE and immunoblotted with indicated antibodies.

Immunofluorescence Staining.

Cells grown on coverslips were fixed in 4% paraformaldehyde for 15 min at RT. Slides were washed in phosphate-buffered saline and blocked with 5% goat serum for 1 hr at room temperature, then incubated with primary antibody mouse anti-Akt (Cell signaling) and rabbit anti-HEATR1 at 37° C. for 30 min. After washing with PBS twice, cells were incubated with FITC or rhodamine-conjugated secondary antibodies at 37° C. for 30 min. Nuclei were counterstained with 4'6-diamidino-2-phenylindole (DAPI). After a final wash with PBS, coverslips were mounted with glycerin containing paraphenylenediamine and examined using confocal microscopy.

Example II

HEATR Regulates Pancreatic Cancer Cells Response to Chemotherapy.

Several genome wide association studies were performed by others to identify genes whose expression associates with sensitivity to chemotherapy. (See, 26 as an example). Surprisingly, the HEATR1 gene was not among the top hits in these studies therefore it was not identified as relevant to responses to chemotherapeutic drugs including Gemcitabine and 1-beta-d-arabinofuranosylcytosine. In contrast, the inventors showed that HEATR1 expression levels associated with responses to several drugs, including Gemcitabine and 1-beta-d-arabinofuranosylcytosine.

HEATR1 was then depleted with siRNA in cells and treated cells with Gemcitabine. Downregulation of HEATR1 resulted in increased resistance to Gemcitabine (FIG. 1A). Similar results were obtained with two HEATR1 specific shRNAs (FIG. 1B and FIG. 7A). Next, multiple classes of chemotherapeutic drugs including oxaliplatin, SN-38, mitomycin c (MMC), paclitaxel, Camptothecin and etopside were used to treat cells. Similarly, cells with HEATR1 knockdown were significantly resistant to these drugs (FIG. 1C and FIG. 7B). These results establish a role of HEATR1 in regulating chemo-response to different anti-tumor agents.

Example III

HEATR1 Regulates Akt Phosphorylation at Thr308 by Promoting Akt-PP2AB56β Interaction.

Because Gemcitabine induced stronger apoptosis activity in control cells than in cells transfected with HEATR1 shRNA (FIG. 8A), the inventors' sought a link between pathways regulating cell death and HEATR1 affects on chemotherapy responses. Gemcitabine induced strong expression of c-PARP1 in control cells than in cells transfected with HEATR1 shRNA as shown by a reduction of c-PARP1 (FIG. 7A). In particular, two HEATR1 specific shRNAs demonstrated that by reducing HEATR1 in Gemcitabine treated cells then c-PARP1 was also reduced as is the amount of apoptosis thus allowing increased cell numbers (FIG. 7B).

Further, we found that downregulation of HEATR1 led to an increased phosphorylation of Akt at Thr308, but not at Ser473 (FIG. 2A-B). These results suggest that depletion of HEATR1 affects steady state Akt phosphorylation, which is consistent with an increase in cell growth (FIG. 7B). We next examined how HEATR1 affects acute Akt activation. Cells were starved and stimulated with serum. Phosphorylation of Akt Thr308 and the Akt substrate GSK-3β were significantly increased in cells transfected with HEATR1 siRNA (FIG. 2C). Furthermore, overexpression of HEATR1 decreased phosphorylation of Akt at Thr308, but not Ser473 (FIG. 2D). We also found that HEATR1 interacted with Akt in cells (FIG. 2E-F). The intracellular co-localization of HEATR1 and Akt were detected by confocal microscopy. Akt and HEATR1 colocalize in the cytoplasm and occasionally at the cell membrane in most cells examined (FIG. 9A).

Since HEATR1 specifically regulates phosphorylated at Thr308, signaling events that directly control Akt phosphorylation at Thr308 were identified during the development of the present inventions. Thr308 of Akt can be phosphorylated by PDK1 and dephosphorylated by PP2A (16, 18, 27). However, no apparent difference of PDK1 (FIG. 2C). HEATR1 neither interacted with PDK1 nor affected the interaction between Akt and PDK1 (FIG. 9B-C), indicating HEATR1 regulates Akt activity independent of PDK1. Next, we examined whether HEATR1 regulates Thr308 phosphorylation through PP2A. Treatment of PP2A inhibitor okadaic acid significantly increased Akt phosphorylation at Thr308, and HEATR1 knockdown did not further increase Thr308 phosphorylation (FIG. 9D).

As shown in FIG. 2G, HEATR1 interacted with PP2A scaffolding subunit Aα, catalytic subunit Cα and regulatory subunits B55α and B56β, which have been reported to specifically target Akt Thr308 dephosphorylation (16-18, 27). Furthermore, purified HEATR1 only interacted with recombinant GST-B56β, suggesting a direct interaction between HEATR1 and B56β (FIG. 2H). Because HEATR1 interacts with both Akt and B56β and regulates Akt phosphorylation, we hypothesized that HEATR1 may function as a scaffolding protein to facilitate Akt dephosphorylation by PP2A. Downregulation of HEATR1 decreased the interaction between B56β and Akt (FIG. 2I), while HEATR1 overexpression increased it (FIG. 2J). Furthermore, purified FLAG-HEATR1 increased the interaction between recombinant His-Akt1 and GST-B56β (FIG. 2K). These results suggest that HEATR1 promotes the interaction between Akt and PP2A, facilitating the dephosphorylation of Akt at Thr308.

Example IV

HEATR1 Regulates Akt Phosphorylation and Cell Response to Gemcitabine Through its Scaffolding Function.

To investigate specific regions of HEATR1 for Akt and B56β interaction, we generated deletion mutants of HEATR1 (FIG. 3A). N-terminal region (aa 1-420) was essential for the binding of HEATR1 with B56β; while the middle region (420-1420) was responsible for the binding of HEATR1 with Akt (FIG. 3B-C). These results suggest that HEATR1 binds Akt and B56β using different regions. To further confirm that the scaffolding function of HEATR1 is related to the regulation of Akt phosphorylation, we overexpressed WT and mutants in cells (FIG. 3D). WT decreased Akt phosphorylation at Thr308 and cellular sensitivity to Gemcitabine, while HEATR1 mutants that abolish Akt or B56β interaction failed to do so (FIG. 3D-E). These results suggest that HEATR1 regulates Akt phosphorylation and cell response to Gemcitabine through its scaffolding function.

Example V

Akt Inhibitor Sensitizes Pancreatic Cells with HEATR1 Knockdown to Gemcitabine.

The results described above suggest that HEATR1 regulates Gemcitabine sensitivity at least partly through regulating Akt and hyperactivation of Akt in cells with low HEATR1 level might be responsible for increased chemoresistance. If this was the case, treating cells with an Akt inhibitor should reverse chemoresistance in cells depleted of HEATR1. TCN-P, the active metabolite of Akt inhibitor triciribine (TCN), binds to PH domain of Akt and prevents its recruitment to cell membrane, where Akt is phosphorylated by PDK1 at Thr308 (28). When TCN was used alone, no significant difference of cytotoxicity and apoptosis was observed in different cell lines transfected with control and HEATR1 siRNA (FIG. 10A-E). In addition, TCN did not significantly affect Gemcitabine sensitivity and apoptosis in control cells. However, TCN sensitized cells depleted of HEATR1 to Gemcitabine (FIG. 4A-B; FIG. 10B-E). We next tested whether addition of TCN would reverse chemoresistance of tumors with low HEATR1 level in vivo. Xenograft experiments showed that downregulation of HEATR1 promoted tumor growth and resistance to Gemcitabine (FIG. 4C-E and FIG. 10F). TCN treatment resensitized these cells' response to Gemcitabine. This is consistent with in vitro results using pancreatic cancer cell lines and indicates that HEATR1 affects chemosensitivity through regulating Akt activity in vivo.

Example VI

Association of HEATR1 Expression, with Our without Corresponding pAKT308 Levels in Pancreatic Cancer Patients, with Survival and Response to Chemotherapy.

Clinical samples were used to examine the role of HEATR1 in clinical responses. Among 100 patients with PDAC, 76 patients died and 24 patients survived, with the median survival time of 18 months. Pathological analysis using pancreatic ductal adenocarcinoma and peritumoral tissues from patients were performed. Statistical analysis revealed that expression of HEATR1 was significantly lower in pancreatic tumor tissue than in normal pancreatic tissues (FIG. 5A). The staining of Akt phosphorylation at Thr308 was significantly higher in pancreatic tumor tissue than in normal pancreatic tissue (FIG. 5A). Furthermore, low HEATR1 proteins levels correlates with increased Akt phosphorylation at Thr308 in representative pancreatic cancer samples (FIG. 5B). We next evaluated whether HEATR1 expression was associated with the response of patients to standardized Gemcitabine chemotherapy. As shown in FIG. 5C-D; FIG. 11 and Table 1, PDAC patients with high HEATR1 or low AktT308 expression in tumors had a significant improvement in overall survival. Thus, determination of HEATR1 expression in PDAC tissues may be useful as an independent predictor for Gemcitabine response. Based on IOD value, we observed a negative correlation between HEATR1 expression and Akt phosphorylation at Thr308 in tumor tissues (FIG. 5E). Meanwhile, we observed a significant correlation between the Akt308 phosphorylation and TNM staging, lymph node metastasis, whereas we did not find the correlation between HEATR1 expression and clinical pathological feature (Table 2). From multivariate survival analysis, HEATR1 expression and Akt308 phosphorylation might be independent prognostic factors among these variables (Table 3). Overall, these results showed that HEATR1 negatively regulates Akt activation and upregulation of Akt activity by loss of HEATR1 in pancreatic cancers might give rise to the resistance to chemotherapy (FIG. 6).

All publications and patents mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in medicine, oncology, molecular biology, cell biology, genetics, or related fields are intended to be within the scope of the following claims.

The invention claimed is:

1. A method, comprising:
   a) obtaining a tissue sample from a subject having pancreatic ductal adenocarcinoma cancer and undergoing therapy with a first chemotherapeutic agent, said tissue sample comprising pancreatic cancer cells,
   b) measuring a lower level of the heat repeating region 1 (HEATR1) biomarker in said pancreatic cancer cells compared to a control; and
   c) changing said therapy to a combination therapy that comprises one or both of administering i) a Akt308 inhibitor and said first chemotherapeutic agent, and ii) said Akt308 inhibitor and a second chemotherapeutic agent that is not the same as said first chemotherapeutic agent,
   said Akt308 inhibitor inhibits Akt308 phosphorylation.

2. The method of claim 1, wherein said combination therapy comprises said i) administering said Akt308 inhibitor and said first chemotherapeutic agent.

3. The method of claim 1, wherein said combination therapy comprises said ii) administering said Akt308 inhibitor and said second chemotherapeutic agent.

4. The method of claim 1, wherein said combination therapy comprises administering said Akt308 inhibitor, said first chemotherapeutic agent, and said second chemotherapeutic agent.

5. The method of claim 1, wherein said pancreatic ductal adenocarcinoma cancer of said subject undergoing said therapy with said first chemotherapeutic agent exhibits resistance to Gemcitabine.

6. The method of claim 5, wherein said combination therapy comprises Triciribine and Gemcitabine.

7. The method of claim 1, wherein said first chemotherapeutic agent is selected from the group consisting of Gemcitabine, 1-beta-d-arabinofuranosylcytosine (Ara C), oxaliplatin, mitomycin C (MMC), 7-ethyl-10-hydroxycamptothecin (SN-38), etoposide, Camptothecin, paclitaxel and cisplatin.

8. The method of claim 1, wherein said second chemotherapeutic agent is selected from the group consisting of Gemcitabine, 1-beta-d-arabinofuranosylcytosine (Ara C), oxaliplatin, mitomycin C (MMC), 7-ethyl-10-hydroxycamptothecin (SN-38), etoposide, Camptothecin, paclitaxel and cisplatin.

* * * * *